United States Patent
Gudmundson et al.

(10) Patent No.: US 8,116,428 B2
(45) Date of Patent: Feb. 14, 2012

(54) METHOD AND APPARATUS FOR ASSESSING CHARACTERISTICS OF LIQUIDS

(75) Inventors: Dan Gudmundson, Quebec (CA); Aidan Doyle, Quebec (CA); Stephan Georgiev, St-Hubert (CA); Vinh Phuc Pham, Donnacona (CA)

(73) Assignee: Optosecurity Inc., Quebec, Quebec (CA)

( * ) Notice: Subject to any disclaimer, the term of this patent is extended or adjusted under 35 U.S.C. 154(b) by 65 days.

(21) Appl. No.: 12/311,031

(22) PCT Filed: Sep. 17, 2007

(86) PCT No.: PCT/CA2007/001658
§ 371 (c)(1),
(2), (4) Date: Mar. 17, 2009

(87) PCT Pub. No.: WO2009/024818
PCT Pub. Date: Feb. 26, 2009

(65) Prior Publication Data
US 2010/0002834 A1 Jan. 7, 2010

Related U.S. Application Data

(60) Provisional application No. 60/825,993, filed on Sep. 18, 2006, provisional application No. 60/826,752, filed on Sep. 25, 2006, provisional application No. 60/893,516, filed on Mar. 7, 2007, provisional application No. 60/917,235, filed on May 10, 2007.

(51) Int. Cl.
*G01N 23/06* (2006.01)
*G01N 23/04* (2006.01)

(52) U.S. Cl. .......................................... 378/53; 378/57

(58) Field of Classification Search .............. 378/50–57, 378/62, 70, 83, 89
See application file for complete search history.

(56) References Cited

U.S. PATENT DOCUMENTS

| | | | |
|---|---|---|---|
| 3,589,511 A | 6/1971 | Britt |
| 3,609,045 A | 9/1971 | Stein |
| 3,673,394 A | 6/1972 | Hartman |
| 4,392,237 A | 7/1983 | Houston |
| 4,454,949 A | 6/1984 | Flum |
| 4,864,142 A | 9/1989 | Gomberg |
| 4,870,666 A | 9/1989 | Lonn et al. |
| 4,962,515 A | 10/1990 | Kopans |
| 4,974,247 A | 11/1990 | Friddell |
| 4,985,906 A | 1/1991 | Arnold |
| 5,044,002 A | 8/1991 | Stein |

(Continued)

FOREIGN PATENT DOCUMENTS

CA 2574402 1/2006

(Continued)

OTHER PUBLICATIONS

Office Action mailed on Jul. 29, 2009 in connection with Canadian Patent Application 2,651,728.

(Continued)

*Primary Examiner* — Irakli Kiknadze

(57) ABSTRACT

A method to perform security screening at an airport on hand-carried baggage. The method includes requesting passengers with hand carried baggage to remove from the baggage a container that holds a liquid and perform an x-ray inspection on the hand carried baggage and on the container while the container remains outside the baggage. According to the method, the results of the x-ray inspection are used to determine if the baggage contains illegal objects and if the liquid is a security threat.

47 Claims, 28 Drawing Sheets

U.S. PATENT DOCUMENTS

| | | | |
|---|---|---|---|
| 5,056,124 A | 10/1991 | Kakimoto et al. | |
| 5,400,381 A | 3/1995 | Steude et al. | |
| 5,428,657 A | 6/1995 | Papanicolopoulos et al. | |
| 5,442,672 A | 8/1995 | Bjorkholm et al. | |
| 5,490,218 A | 2/1996 | Krug et al. | |
| 5,557,108 A | 9/1996 | Tumer | |
| 5,568,262 A | 10/1996 | LaChappelle et al. | |
| 5,600,303 A | 2/1997 | Husseiny et al. | |
| 5,600,700 A | 2/1997 | Krug et al. | |
| 5,692,029 A | 11/1997 | Husseiny et al. | |
| 5,768,334 A | 6/1998 | Maitrejean et al. | |
| 5,838,758 A | 11/1998 | Krug et al. | |
| 5,864,600 A | 1/1999 | Gray et al. | |
| 6,018,562 A | 1/2000 | Willson | |
| 6,026,171 A | 2/2000 | Hiraoglu et al. | |
| 6,054,712 A | 4/2000 | Komardin et al. | |
| 6,069,936 A | 5/2000 | Bjorkholm | |
| 6,542,574 B2 | 4/2003 | Grodzins | |
| 6,654,445 B2 | 11/2003 | Shepherd et al. | |
| 6,707,381 B1 | 3/2004 | Maloney | |
| 6,707,879 B2 | 3/2004 | McClelland et al. | |
| 6,721,387 B1 | 4/2004 | Naidu et al. | |
| 6,721,391 B2 | 4/2004 | McClelland et al. | |
| 6,763,083 B2 | 7/2004 | Fernandez | |
| H2110 H | 10/2004 | Newman | |
| 6,840,120 B2 | 1/2005 | Sakairi et al. | |
| 6,952,163 B2 | 10/2005 | Huey et al. | |
| 7,065,175 B2 | 6/2006 | Green | |
| 7,092,485 B2 | 8/2006 | Kravis | |
| 7,164,750 B2 | 1/2007 | Nabors et al. | |
| 7,257,188 B2 | 8/2007 | Bjorkholm | |
| 7,274,768 B2 | 9/2007 | Green | |
| 7,317,390 B2 | 1/2008 | Huey et al. | |
| 7,355,402 B1 | 4/2008 | Taicher et al. | |
| 7,386,093 B2 | 6/2008 | Wu et al. | |
| 7,614,788 B2 | 11/2009 | Gatten | |
| 7,789,401 B2 | 9/2010 | Ambrefe, Jr. | |
| 2001/0033636 A1 | 10/2001 | Hartick et al. | |
| 2003/0062373 A1 | 4/2003 | Holland | |
| 2004/0016271 A1 | 1/2004 | Shah et al. | |
| 2004/0101097 A1 | 5/2004 | Wakayama et al. | |
| 2004/0252024 A1* | 12/2004 | Huey et al. | 340/540 |
| 2005/0036689 A1 | 2/2005 | Mahdavieh | |
| 2005/0058242 A1 | 3/2005 | Peschmann | |
| 2005/0111618 A1 | 5/2005 | Sommer, Jr. et al. | |
| 2005/0117700 A1 | 6/2005 | Peschmann | |
| 2005/0173284 A1 | 8/2005 | Ambrefe | |
| 2005/0193648 A1 | 9/2005 | Klein et al. | |
| 2006/0078085 A1 | 4/2006 | Zanker | |
| 2006/0086794 A1 | 4/2006 | Knowles et al. | |
| 2006/0115044 A1 | 6/2006 | Wu et al. | |
| 2006/0193434 A1 | 8/2006 | Green | |
| 2006/0203960 A1 | 9/2006 | Schlomka et al. | |
| 2006/0257005 A1 | 11/2006 | Bergeron et al. | |
| 2007/0003009 A1 | 1/2007 | Gray | |
| 2007/0013519 A1 | 1/2007 | Chung et al. | |
| 2007/0041612 A1 | 2/2007 | Perron et al. | |
| 2007/0041613 A1 | 2/2007 | Perron et al. | |
| 2007/0058037 A1 | 3/2007 | Bergeron et al. | |
| 2007/0132580 A1 | 6/2007 | Ambrefe | |
| 2007/0133743 A1 | 6/2007 | Johnson et al. | |
| 2007/0192850 A1 | 8/2007 | Cowburn | |
| 2007/0217571 A1 | 9/2007 | Teslyar et al. | |
| 2007/0297560 A1* | 12/2007 | Song et al. | 378/4 |
| 2008/0056443 A1* | 3/2008 | Hu et al. | 378/54 |
| 2008/0062262 A1 | 3/2008 | Perron et al. | |
| 2008/0116267 A1 | 5/2008 | Barber | |
| 2008/0138475 A1 | 6/2008 | Heuft | |
| 2008/0152082 A1 | 6/2008 | Bouchard et al. | |
| 2008/0170660 A1 | 7/2008 | Gudmundson et al. | |
| 2008/0240578 A1 | 10/2008 | Gudmundson et al. | |
| 2008/0312768 A1 | 12/2008 | Ewing et al. | |
| 2009/0060135 A1 | 3/2009 | Morton | |
| 2009/0146061 A1 | 6/2009 | Manneschi | |
| 2009/0168963 A1 | 7/2009 | Harding | |
| 2009/0196396 A1 | 8/2009 | Doyle et al. | |
| 2010/0027741 A1 | 2/2010 | Doyle et al. | |
| 2011/0007870 A1 | 1/2011 | Roux et al. | |

FOREIGN PATENT DOCUMENTS

| | | |
|---|---|---|
| CA | 2623812 | 5/2007 |
| CA | 2676913 | 11/2010 |
| CA | 2666838 | 12/2010 |
| GB | 2420683 | 5/2006 |
| GB | 2 441 551 | 12/2008 |
| JP | 2006-214725 | 8/2006 |
| WO | WO 03/052398 | 6/2003 |
| WO | WO/2006/119603 | 11/2006 |
| WO | PCT/CA2007/001658 | 1/2008 |
| WO | PCT/CA2007/001749 | 1/2008 |
| WO | WO 2008/009134 | 1/2008 |
| WO | PCT/CA2007/001658 | 9/2008 |
| WO | PCT/CA2008/001591 | 11/2008 |
| WO | PCT/CA2007/001658 | 12/2008 |
| WO | PCT/CA2008/001721 | 12/2008 |
| WO | PCT/CA2008/001792 | 12/2008 |
| WO | 2009/024818 | 2/2009 |
| WO | PCT/CA2008/002025 | 6/2009 |
| WO | PCT/CA2009/000395 | 7/2009 |
| WO | PCT/CA2009/000401 | 8/2009 |
| WO | 2009127353 | 10/2009 |
| WO | PCT/CA2009/000811 | 11/2009 |
| WO | WO 2010/028474 A1 | 3/2010 |
| WO | PCT/CA2008/001591 | 9/2010 |
| WO | PCT/CA2010/000916 | 9/2010 |
| WO | PCT/CA2010/001200 | 11/2010 |
| WO | 2010/145016 | 12/2010 |

OTHER PUBLICATIONS

Office Action mailed on Jul. 10, 2009 in connection with Canadian Patent Application 2,666,838.

Office Action mailed on Nov. 3, 2009 in connection with Canadian Patent Application 2,666,838.

Office Action mailed on Jan. 28, 2010 in connection with Canadian Patent Application 2,676,913.

Freud et al., "Simulation of X-ray NDT Imaging Techniques", http://www.ndt.net/article/wcndt00/papers/idn256/idn256.htm, Dec. 3, 2009.

Xie et al., "Simulation of X-ray Imaging Systems for Luggage Inspection", The Bradley Department of Electrical and Computer Engineering, Virginia Polytechnic Institute and State University, Blacksburg Virginia 26061-0111, p. 248-253.

Freud et al., "Simulation of X-ray NDT Imaging Techniques", Proceedings of the 15th World Conference on Non-Destructive Testing, Rome, Oct. 15-21, 2000, http://www.ndt.net/article/wcndt00/papers/idn256/idn256.htm, pages consulted on Dec. 3, 2009.

Xie et al., "Simulation of X-ray Imaging Systems for Luggage Inspection", Second Explosives Detection Symposium and Aviation Security Conference, Nov. 12-15, 1996, p. 248-253.

Benjamin, R., "Object-Based 3D X-Ray Imaging for Second-line Security Screening", London, 1995, (Abstract).

PinPoint TM Threat Identification Software, http://www.guardiantechintl.com/security.php?npage=pinpoint, Jul. 25, 2005.

"Secure Flight Passenger Screening Program", http://www.globalsecurity.org/security/systems/passenger_screen.htm, Oct. 28, 2005.

Optosecurity, "Security Technology Overview: Advanced Vehicle Verification & Threat Identification", 1 p.

Airport Magazine, Solutions, Products, Services, vol. 7, Mar. 2006, 5 p.

Written Opinion of the International Searching Authority mailed on Jan. 14, 2008 in connection with International Patent Application No. PCT/CA2007/001749, 4 pages.

International Preliminary Report on Patentability completed on Feb. 1, 2010 in connection with International Patent Application No. PCT/CA2008/001792, 3 pages.

Office Action issued by the Canadian Intellectual Property Office on Jan. 28, 2010 in connection with Canadian Patent Application No. 2,666,838, 5 pages.

Office Action issued by the Canadian Intellectual Property Office on Mar. 2, 2010 in connection with Canadian Patent Application No. 2,676,903, 4 pages.

Office Action issued by the Canadian Intellectual Property Office on Mar. 19, 2010 in connection with Canadian Patent Application No. 2,651,728, 2 pages.

Office Action issued by the Canadian Intellectual Property Office on Mar. 31, 2010 in connection with Canadian Patent Application No. 2,690,163, 3 pages.

International Preliminary Report on Patentability mailed on Apr. 15, 2010 in connection with International Patent Application No. PCT/CA2008/001721, 7 pages.

Office Action issued by the Canadian Intellectual Property Office on May 5, 2010 in connection with Canadian Patent Application No. 2,676,913, 2 pages.

Office Action issued by the Canadian Intellectual Property Office on May 14, 2010 in connection with Canadian Patent Application No. 2,690,831, 3 pages.

Office Action issued by the Canadian Intellectual Property Office on Jun. 7, 2010 in connection with Canadian Patent Application No. 2,692,662, 3 pages.

Office Action issued by the Canadian Intellectual Property Office on Jun. 28, 2010 in connection with Canadian Patent Application No. 2,697,525, 3 pages.

Office Action issued by the Canadian Intellectual Property Office on Jun. 30, 2010 in connection with Canadian Patent Application No. 2,696,031, 2 pages.

Page, D. L. et al., "Perception-based 3D Triangle Mesh Segmentation Using Fast Marching Watersheds.", Proc. Intl. Conf. on Computer Vision and Pattern Recognition, vol. II, pp. 27-32, Madison, WI, Jun. 2003.

Examiner's Report mailed on Jan. 31, 2011 in connection with Canadian Patent Application 2,697,525, 2 pages.

Office Action mailed on Feb. 10, 2011 in connection with U.S. Appl. No. 12/680,622, 10 pages.

Office Action mailed on Feb. 8, 2011 in connection with U.S. Appl. No. 12/385,253, 14 pages.

Office Action mailed on Feb. 9, 2011 in connection with U.S. Appl. No. 12/311,522, 11 pages.

International Preliminary Report on Patentability dated Jan. 12, 2011 in connection with PCT application PCT/CA2009/000401, 15 pages.

Office Action mailed on Aug. 5, 2010 in connection with U.S. Appl. No. 12/385,253, 18 pages.

Office Action mailed on Aug. 12, 2010 in connection with U.S. Appl. No. 12/311,522, 30 pages.

Office Action mailed on Aug. 31, 2010 in connection with Canadian patent application 2,690,831, 2 pages.

Office Action mailed on Aug. 31, 2010 in connection with Canadian patent application 2,692,662, 3 pages.

Office Action mailed on Oct. 6, 2010 in connection with Canadian Patent Application 2,696,031—2 pages.

Office Action mailed on Oct. 29, 2010 in connection with Canadian Patent Application 2,651,728—6 pages.

Office Action mailed on Oct. 28, 2010 in connection with Canadian Patent Application 2,676,903—2 pages.

Office Action mailed on Nov. 2, 2010 in connection with Canadian Patent Application 2,690,163—1 page.

Office Action mailed on Nov. 17, 2010 in connection with Canadian Patent Application 2,709,468—2 pages.

Examiner's Report mailed on Mar. 29, 2011 in connection with Canadian Patent Application 2,725,626, 5 pages.

Examiner's Report mailed on Mar. 29, 2011 in connection with Canadian Patent Application 2,690,831, 2 pages.

Office Action mailed on May 2, 2011 in connection with Canadian patent application 2,692,662—3 pages.

European Search Report mailed on Jun. 9, 2011 in connection with European patent application No. EP2007815851.6, 6 Pages.

Gao et al., "Application of X-ray CT to liquid security inspection: System analysys and beam hardening correction", Nuclear Instruments & Methods in Physics Research, Section—A:Accelerators, Spectrometers, Detectors and Associated Equipement, Elsevier, Amsterdam, NL, vol. 579, No. 1, pp. 395-399, Aug. 8, 2007.

International Preliminary Report on Patentability mailed completed on Oct. 24, 2011 in connection with International Patent Application PCT/CA2010/000916, 17 pages.

Examiner's Report mailed on Sep. 2, 2011 in connection with Canadian Patent Application 2,737,075, 3 pages.

* cited by examiner

| UPC bar code | Density | Effective atomic number | Container features | Diffraction/ backscatter signature | Product identification | Threat status |
|---|---|---|---|---|---|---|
| 1001...001 | | | | | Toothpaste brand Z | Safe |
| 0011...110 | | | | | Orange juice brand Y | Safe |
| 1100...111 | | | | | Shampoo brand X | Safe |
| 1100...000 | | | | | Acid | Unsafe |

METHOD AND APPARATUS FOR ASSESSING CHARACTERISTICS OF LIQUIDS

FIELD OF THE INVENTION

The present invention relates to technologies for assessing properties of liquids, in particular determining if a liquid presents a security threat. The invention has numerous applications, in particular it can be used for scanning hand carried baggage at airport security check points.

BACKGROUND OF THE INVENTION

Some liquids or combinations of liquids and other compounds may cause enough damage to bring down an aircraft. As no reliable technology-based solution currently exists to adequately address this threat, authorities have implemented a ban of most liquids, gels and aerosols in cabin baggage.

As a result, there have been disruptions in operations (e.g., a longer screening process; changed the focus for screeners; additional line-ups), major inconveniences for passengers (as well as potential health hazards for some) and economic concerns (e.g., increased screening costs; lost revenues for airlines and duty free shops; large quantities of confiscated—including hazardous—merchandise to dispose of), and so on.

Clearly, there is a need to provide a technology-based solution to address the threat of fluids that are flammable, explosive or commonly used as ingredients in explosive or incendiary devices.

SUMMARY OF THE INVENTION

The invention provides a method to perform security screening at an airport on hand-carried baggage. The method includes requesting passengers with hand carried baggage to remove from the baggage a container that holds a liquid and to perform an x-ray inspection on the hand carried baggage and on the container while the container remains outside the baggage. The results of the x-ray inspection are used to determine:
1. if the baggage contains illegal objects;
2. if the liquid is a security threat.

The invention also provides a security screening system to determine if a container holding a liquid presents a security threat. The screening system includes an input for receiving image data conveying an image of the liquid product generated when the liquid product is subjected to penetrating radiation. The screening system also includes a knowledge bank containing a plurality of entries, each entry containing information about one or more liquid characteristics. The screening system further includes a logic module which uses the image data to determine if the liquid in the container can be matched to anyone of the entries and then uses those results to assess if the liquid poses a security threat.

The invention also provides a security screening system to determine if a container bearing a liquid product identification holds a liquid matching that product identification. The screening system has an inspection device for acquiring one or more characteristics of the container and for deriving a response of the liquid to penetrating radiation. The system also includes a knowledge bank containing responses of different commercially available liquids to penetrating radiation, each response mapped to one or more characteristics of a container in which the liquid is packaged and sold in the market. A logic module is also provided for searching the knowledge bank to identify one or more entries matching the one or more characteristics acquired by the characterization module and for comparing the responses of the identified entries to the response of the liquid, the logic module using the results of comparing operation to determine if the liquid in the container matches the product identification on the container.

The invention further provides a security screening system to determine if a container bearing a liquid product identification holds a liquid that poses a security threat. The screening system has a characterization module to acquire one or more characteristics of the container and an inspection device for subjecting the container to penetrating radiation and for deriving a response of the liquid to the penetrating radiation. A knowledge bank is also provided containing responses of different commercially available liquids to penetrating radiation, each response mapped to one or more characteristics of a container in which the liquid is packaged and sold in the market. A logic module searches the knowledge bank to identify one or more entries matching the one or more characteristics acquired by the characterization module and for comparing the responses of the identified entries to the response of the liquid, the logic module using the results of said comparing to determine if the liquid in the container poses a security threat.

The invention also provides a computer readable medium containing a knowledge bank, the knowledge bank having a plurality of entries, each entry comprising:
  a) one or more characteristics of a container in which a liquid is packaged and sold in the market;
  b) a response of the liquid observed when the liquid is subjected to penetrating radiation.

The invention further provides a system for determining a parameter of a liquid in a container, the parameter being selected in the group consisting of density and effective atomic number. The apparatus having an input for receiving X-ray image data representing a two-dimensional X-ray image of the container holding the liquid and a computer based logic module for:
  i) processing the X-ray image data to derive path length information, the path length information being indicative of a length of a path followed by X-rays through the liquid;
  ii) using the path length information to determine the parameter.

The invention further provides a method for determining if a liquid product comprised of a container holding a liquid presents a security threat. The method includes receiving image data conveying an image of the liquid product produced when the liquid product is subjected to penetrating radiation and also providing a knowledge bank storing a plurality of entries, each entry containing information about one or more liquid characteristics. The method further includes using the image data to determine if the liquid in the container can be matched to anyone of the entries and then using the results of the matching operation in assessing if the liquid in the container poses a security threat.

The invention yet provides a method for determining a parameter of a liquid in a container, the parameter being selected in the group consisting of density and effective atomic number. The method includes the steps of receiving X-ray image data representing a two-dimensional X-ray image of the container holding the liquid and processing the X-ray image data with a computer to:
  i) derive path length information, the path length information being indicative of a length of a path followed by X-rays through the liquid;
  ii) determine the parameter by using the path length information.

The invention further provides a system for determining a parameter of a liquid in a container, the parameter being selected in the group consisting of density and effective atomic number. The apparatus has an input for receiving X-ray image data representing a two-dimensional X-ray image of the container holding the liquid and a computer based logic module for:

i) processing the X-ray image data to derive container height information, the container height information being indicative of a length of a path followed by X-rays through the liquid;

ii) using the container height information to determine the parameter.

The invention also provides system for determining a parameter of a liquid in a container, the parameter being selected in the group consisting of density and effective atomic number. The apparatus having an input for receiving X-ray image data representing a two-dimensional X-ray image of the container holding the liquid and a computer based logic module for i) processing the X-ray image data to derive liquid height information indicative of a height of the body of liquid held by the container;

ii) using the liquid height information to determine the parameter.

The invention further provides method for determining a parameter of a liquid in a container, the parameter being selected in the group consisting of density and effective atomic number. The method includes the steps of receiving X-ray image data representing a two-dimensional X-ray image of the container holding the liquid and processing the X-ray image data with a computer to:

i) derive liquid height information indicative of a height of the body of liquid held by the container;

ii) determine the parameter by using the liquid height information.

The invention also provides a system for determining a parameter of a liquid in a container, the parameter being selected in the group consisting of density and effective atomic number. The apparatus includes an input for receiving X-ray image data representing a two-dimensional X-ray image of the container holding the liquid, the X-ray image data conveying compound attenuation information indicating a degree with which X-rays are attenuated by the liquid and by the container walls and a computer based logic module for:

i) processing the X-ray image data to compensate the compound attenuation information for the attenuation due to the container walls and derive attenuation information due to the liquid;

ii) using the attenuation information due to the liquid to derive the parameter.

The invention also provides a security screening system to determine if a liquid product comprised of a container holding a liquid presents a security threat. The screening system having an input for receiving image data conveying an image of the liquid product produced when the liquid product is subjected to penetrating radiation and a display for displaying an image of the liquid product generated on the basis of the image data. The screening system also has a user interface including at least one user interface tool allowing an operator to perform a designation on the display of the container, the designation generating location data identifying an area of the image where the container resides and a logic module to select a portion of the image data on the basis of the location data and to process the selected image data portion to determine if the liquid in the container poses a security threat.

The invention further provides a security screening system to determine if a liquid product comprised of a container holding a liquid presents a security threat. The security screening system including an input for receiving image data conveying an image of the liquid product produced when the liquid product is subjected to penetrating radiation and a display for displaying an image of the liquid product generated on the basis of the image data. The security screening system further including a logic module to process the image data to determine if the liquid in the container poses a security threat, the logic module issuing commands to the display to cause the display to visually enhance a portion of the image where the container resides to make the container visually more distinguishable from other objects appearing in the image.

BRIEF DESCRIPTION OF THE DRAWINGS

A detailed description of examples of implementation of the present invention is provided hereinbelow with reference to the following drawings, in which:

FIG. 1b is a more detailed illustration of the X-ray apparatus of FIG. 1a;

FIG. 19b is a table-like representation of a knowledge bank storing information about liquid products and their associated threat statuses;

FIG. 20 is a set-up for implementing the method shown in FIG. 19a;

Figure 1A:
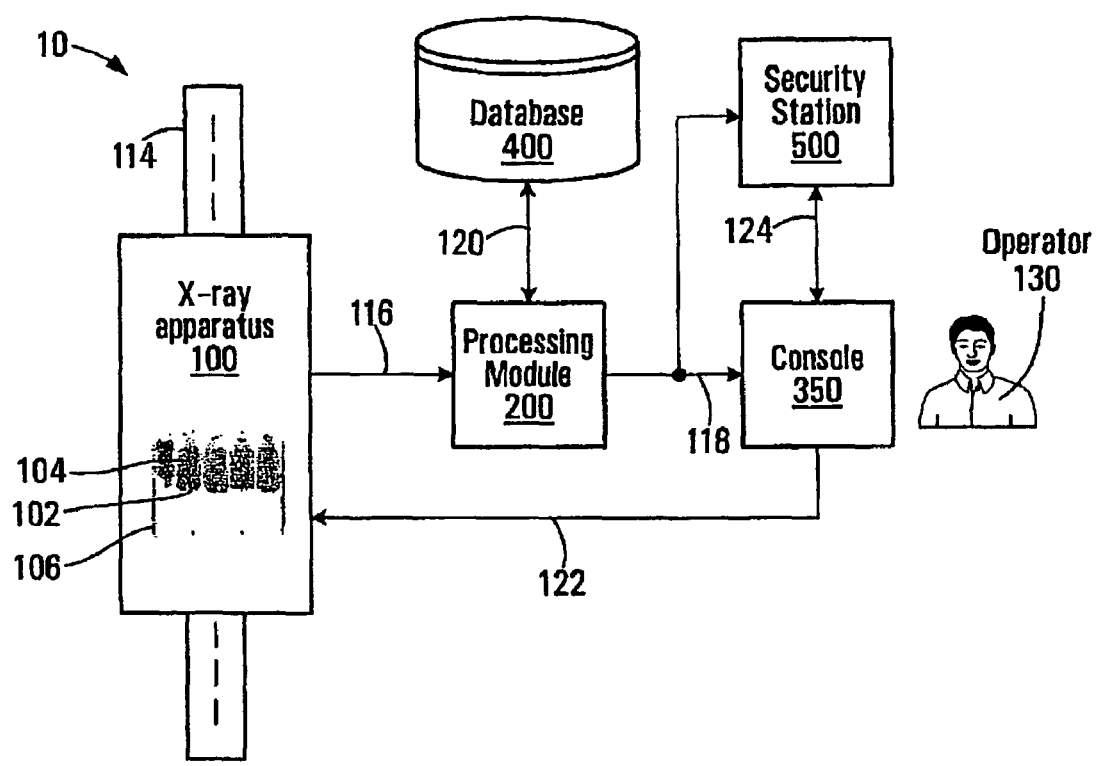
FIG. 1a is a block diagram of an apparatus using X-rays to scan hand carried baggage at a security check point, according to a non-limiting example of implementation of the invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

With reference to FIG. 1a, there is shown a specific non-limiting example of a system 10 for use in screening containers with liquids, in accordance with a non-limiting embodiment of the present invention. The system 10 comprises an x-ray apparatus 100 that applies an x-ray screening process to a liquid 104 (Note that for the purpose of this specification "liquid" refers to a state of matter that is neither gas nor solid and that generally takes the shape of the container in which it is put. This definition would, therefore encompass substances that are pastes or gels, in addition to substances having a characteristic readiness to flow. For instance, toothpaste, and other materials having the consistency of toothpaste would be considered to fall in the definition of "liquid".) contained in a container 102 that is located within a screening area of the x-ray apparatus 100. In an airport setting, a passenger may place the container 102 in a tray 106 which is then placed onto a conveyor 114 that causes the container 102 to enter the screening area of the x-ray apparatus 100. The x-ray apparatus 100 outputs an image signal 116 to a processing module 200.

The processing module 200 may be co-located with the x-ray apparatus 100 or it may be remote from the x-ray apparatus 100 and connected thereto by a communication link, which may be wireless, wired, optical, etc. The processing module 200 receives the image signal 116 and executes a method (to be described later on) to produce a threat assessment 118. The processing module 200 has access to a database 400 which constitutes a knowledge bank via a communication link 120 that may be local to the processing module 200 (e.g., on a common printed circuit board, or connected as a peripheral device thereto by cable or Bluetooth), or which can be remote from the processing module 200 (e.g., connected via a wireline, wireless or optical link that may traverse a data network). The processing module 200 may be implemented using software, hardware, control logic or a combination thereof.

The threat assessment 118 is provided to a console 350 and/or to a security station 500, where the threat assessment 118 can be conveyed to an operator 130 or other security personnel. The console 350 can be embodied as a piece of equipment that is in proximity to the x-ray apparatus 100, while the security station 500 can be embodied as a piece of equipment that is remote from the x-ray apparatus 100. The console 350 may be connected to the security station 500 via a communication link 124 that may traverse a data network (not shown).

The console 350 and/or the security station 500 may comprise suitable software and/or hardware and/or control logic to implement a graphical user interface (GUI) for permitting interaction with the operator 130. Consequently, the console 350 and/or the security station 500 may provide a control link 122 to the x-ray apparatus 100, thereby allowing the operator 130 to control motion (e.g., forward/backward and speed) of the conveyor 114 and, as a result, to control the position of the container 102 within the screening area of the x-ray apparatus 100.

Figure 1B:
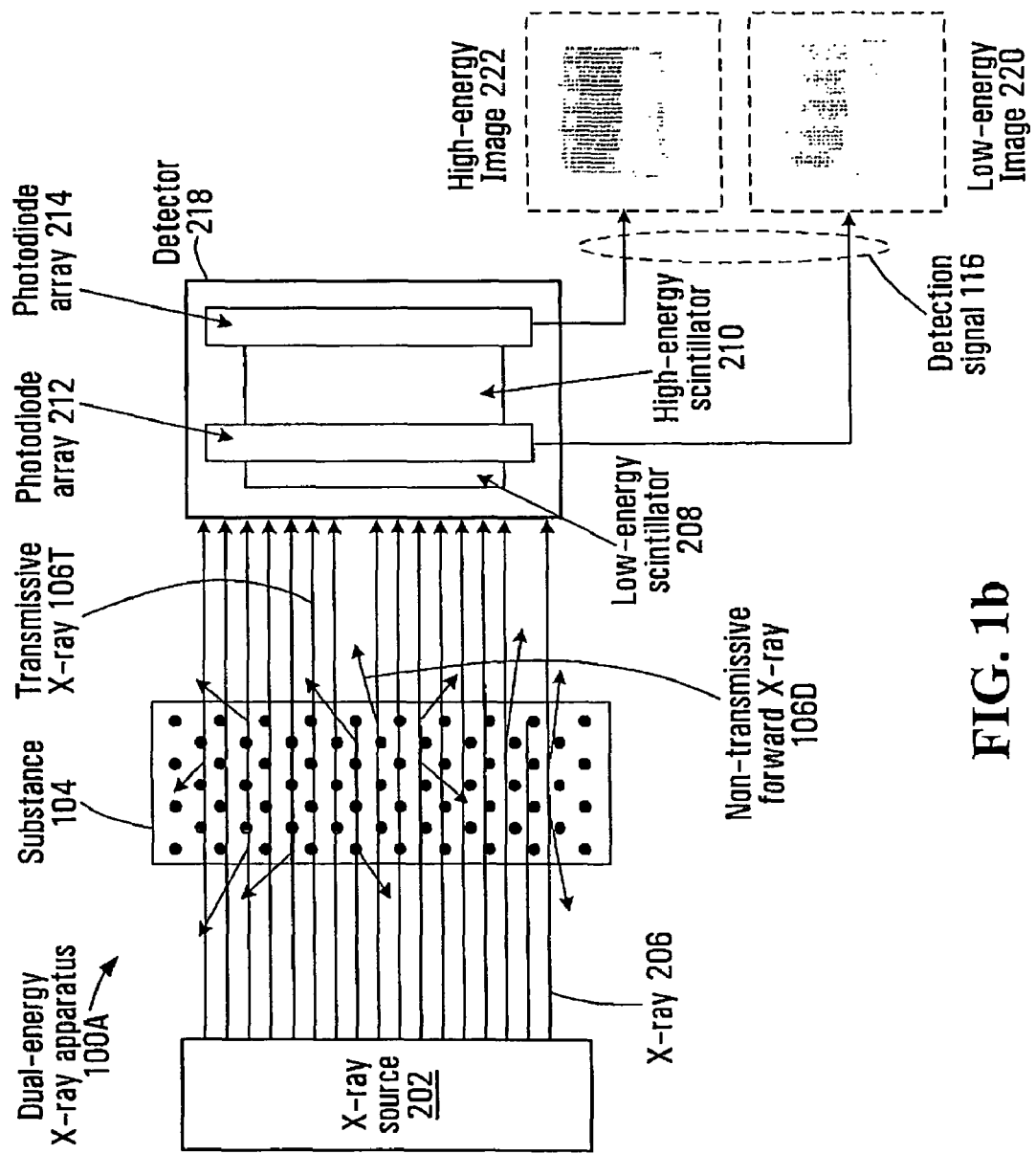

In accordance with a specific non-limiting embodiment, and with reference to FIG. 1b, the x-ray apparatus 100 is a dual-energy x-ray apparatus 100A. However, persons skilled in the art will appreciate that the present invention is not limited to such an embodiment. Continuing with the description of the dual-energy x-ray apparatus 100A, an x-ray source 202 emits x-rays 206 at two distinct photon energy levels, either simultaneously or in sequence. Example energy levels include 50 keV (50 thousand electron-volts) and 150 keV, although persons skilled in the art will appreciate that other energy levels are possible.

Generally speaking, x-rays are typically defined as electromagnetic radiation having wavelengths that lie within a range of 0.001 to 10 nm (nanometers) corresponding to photon energies of 120 eV to 1.2 MeV. Although the electromagnetic radiation referred to primarily throughout this description are x-rays, those skilled in the art will appreciate that the present invention is also applicable to electromagnetic radiation having wavelengths (and corresponding photon energies) outside this range.

Figure 4:
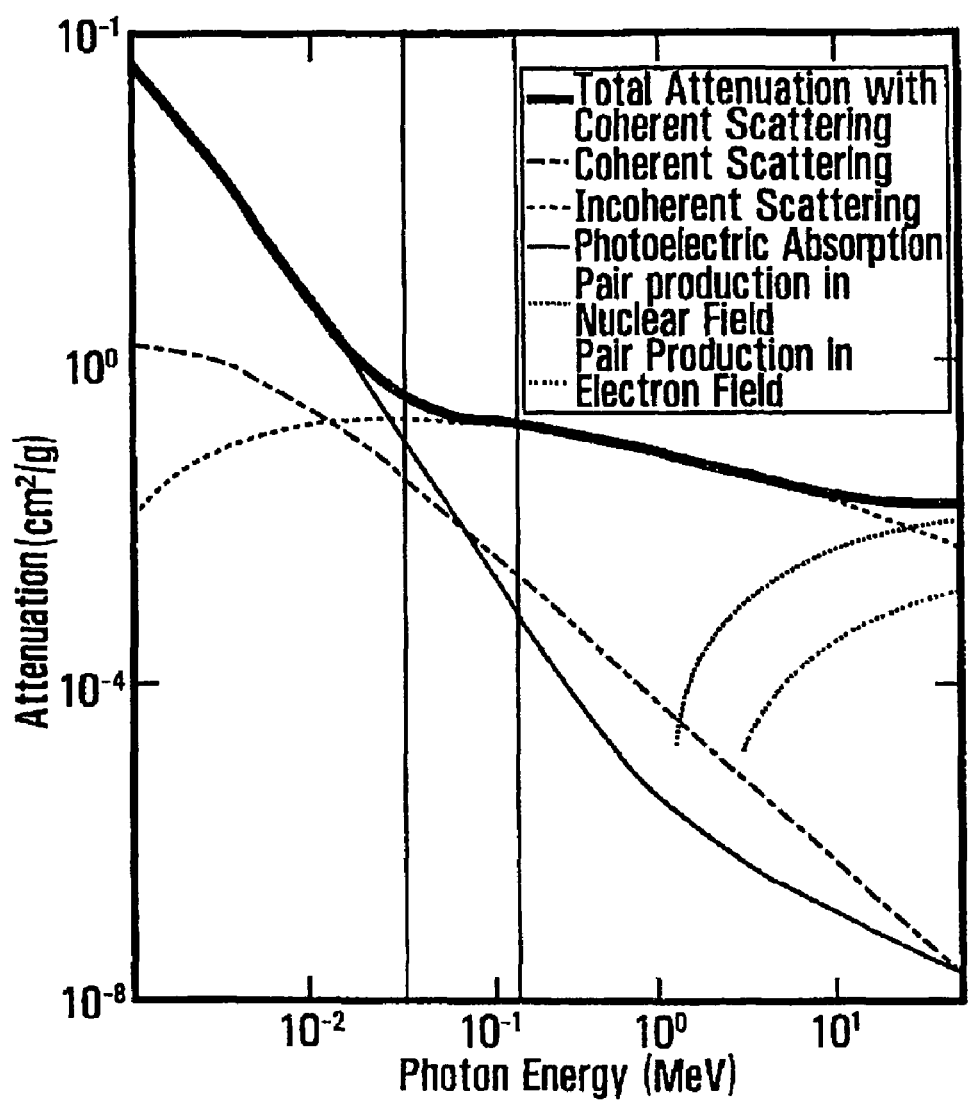
FIG. 4 is graph illustrating the total X-ray attenuation in $H_2O$ due to various X-ray matter interactions.

A detector 218 located generally along an extension of the path of the x-rays 206 receives photons emanating from the combination of the liquid 104 and the container 102 in which it is located. Some of the incoming photons (X-rays 206) will go straight through the container/liquid 104 combination while some will interact with the container/liquid 104 combination. There are a number of interactions possible, such as:

The Rayleigh scattering (coherent scattering)
The photoelectric absorption (incoherent scattering)
The Compton scattering (incoherent scattering)
The pair production;
Diffraction The total attenuation of the contribution of the various X-rays—matter interactions is shown in FIG. 4. In this example the matter is $H_2O$ but the attenuation profile for other materials is generally similar. For today's state-of-the-art security screening systems, the energy levels commonly utilized lie between 50 keV and 150 keV.

Figure 5:
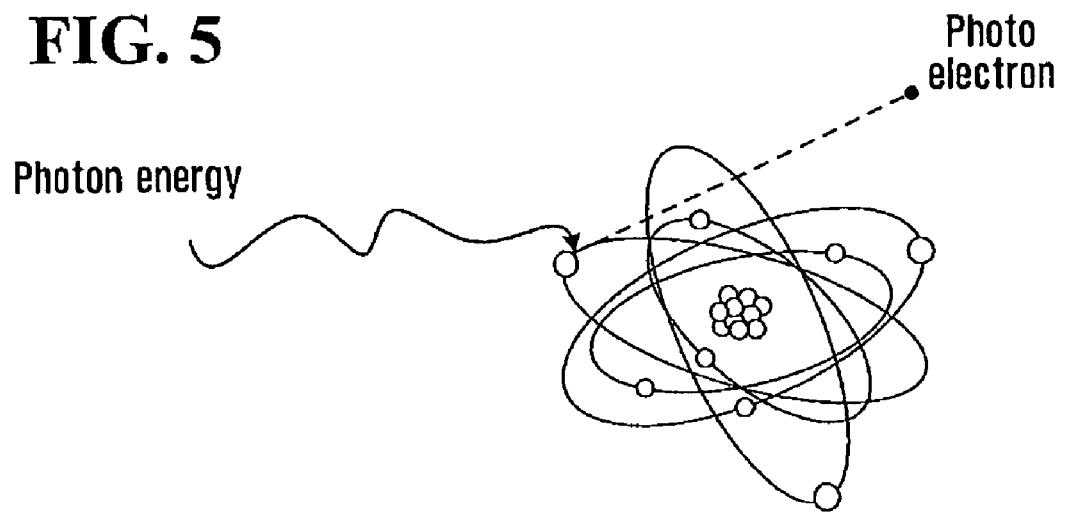
FIG. 5 is a generalized illustration of the photoelectric X-ray absorption process.

The photoelectric absorption (FIG. 5) of X-rays occurs when the X-ray photon is absorbed, resulting in the ejection of electrons from the shells of the atom, and hence the ionization of the atom. Subsequently, the ionized atom returns to the neutral state with the emission of whether an Auger electron or an X-ray characteristic of the atom. This subsequent X-ray emission of lower energy photons is however generally absorbed and does not contribute to (or is hinder) the image making process. This type of X-ray interaction is dependent on the effective atomic number of the material or atom and is dominant for atoms of high atomic numbers. Photoelectron absorption is the dominant process for X-ray absorption up to energies of about 25 keV. Nevertheless, in the energy range of interest for security applications, the photoelectric effect plays a smaller role with respect to the Compton scattering, which becomes dominant.

Figure 6:
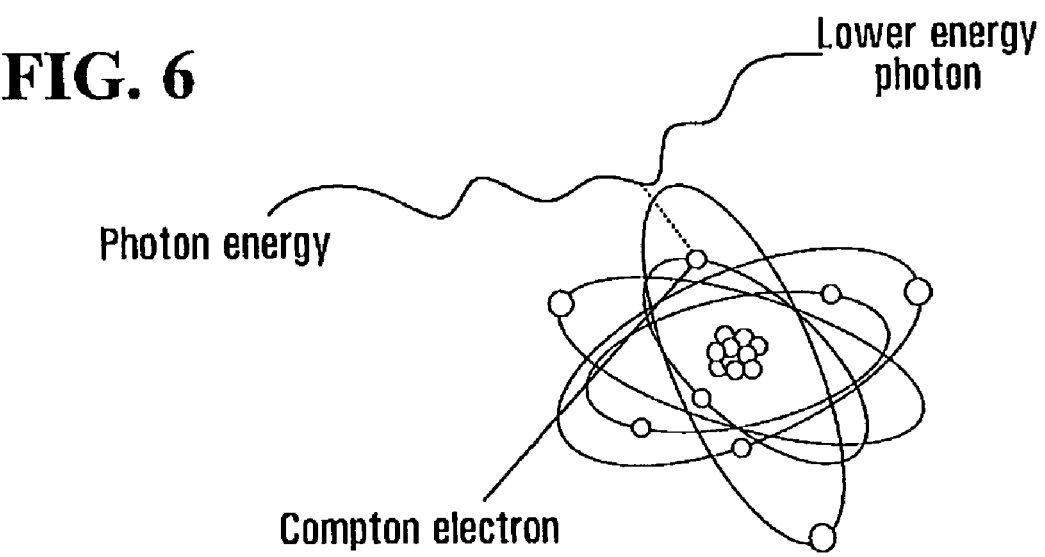
FIG. 6 is a generalized illustration of the Compton scattering effect.

Compton scattering (FIG. 6) occurs when the incident X-ray photon is deflected from its original path by an interaction with an electron. The electron gains energy and is ejected from its orbital position. The X-ray photon looses energy due to the interaction but continues to travel through the material along an altered path. Since the scattered X-ray photon has less energy, consequently it has a longer wavelength than the incident photon. The event is also known as incoherent scattering, because the photon energy change resulting from an interaction is not always orderly and consistent. The energy shift depends on the angle of scattering and not on the nature of the scattering medium. Compton scattering is proportional to material density and the probability of it occurring increases as the incident photon energy increases.

The diffraction phenomenon of the x-rays by a material with which they interact is related to the scattering effect described earlier. When the x-rays are scattered by the individual atoms of the material, the scattered x-rays may then interact and produce diffraction patterns that depend upon the internal structure of the material that is being examined.

The photons received by the detector 218 include photons that have gone straight through the liquid 104 and the container 102; these photons have not interacted in any significant matter with the liquid 104. Others of the received photons have interacted with the liquid 104 or the container.

In accordance with a specific non-limiting embodiment of the present invention, the detector 218 may comprise a low-energy scintillator 208 and a high-energy scintillator 210, which can be made of different materials. The low-energy scintillator 208 amplifies the intensity of the received photons such that a first photodiode array 212 can produce a low-energy image 220. Similarly, the high-energy scintillator 210 amplifies the intensity of the received photons such that a second photodiode array 214 can produce a high-energy image 222. The low-energy image 220 and the high-energy image 222 may be produced simultaneously or in sequence. Together, the low-energy image 220 and the high-energy image 222 form the aforesaid image signal 116.

Referring back to FIG. 1a, the processing module 200 receives the image signal 116 and processes the signal in conjunction with data contained in a knowledge bank 400 to determine if the liquid in the container poses a security threat. The determination can include an explicit assessment as to whether the liquid is a threat or not a threat. Alternatively, the determination can be an identification of the liquid or the class of materials to which the liquid belongs, without explicitly saying whether the liquid is threatening or not threatening. For example, the processing module can determine that the liquid is "water", hence the operator 130 would conclude that it is safe. In a different example, the processing module 200 determines that the liquid belongs to a class of flammable materials, in which case the operator 130 would conclude that it would be a security threat. Also, the determination can be such as to provide an explicit threat assessment and at the same time also provide an identification of the liquid in terms of general class of materials or in terms of a specific material. The results of the determination are conveyed in the threat assessment signal 118 which is communicated to the console 350 and/or the security station 500 where it is conveyed to the operator 130.

Figure 2A:
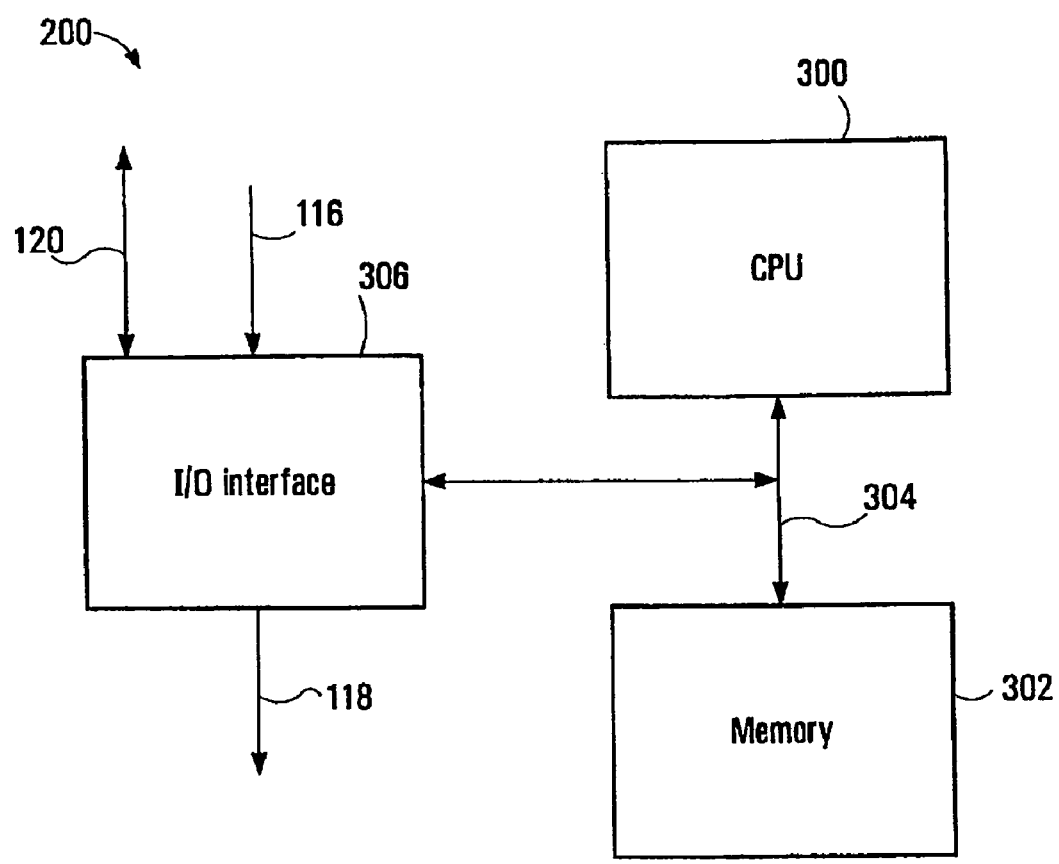
FIG. 2a is a more detailed block diagram of the processing module of the apparatus shown in FIG. 1b.

FIG. 2a is a high level block diagram of the processing module 200. The processing module 200 has a Central Processing Unit (CPU) 300 that communicates with a memory 302 over a data bus 304. The memory 302 stores the software that is executed by the CPU 300 and which defines the functionality of the processing module 200. The CPU 300 exchanges data with external devices through an Input/Output (I/O) interface 306. Specifically, the image signal 116 is received at the I/O interface 306 and the data contained in the signal is processed by the CPU 300. The threat assessment signal 118 that is generated by the CPU 300 is output to the console 350 and/or the security station 500 via the I/O interface 306. Also, communications between the knowledge bank 400 and the processing module 200 are made via the I/O interface 306.

Figure 2B:
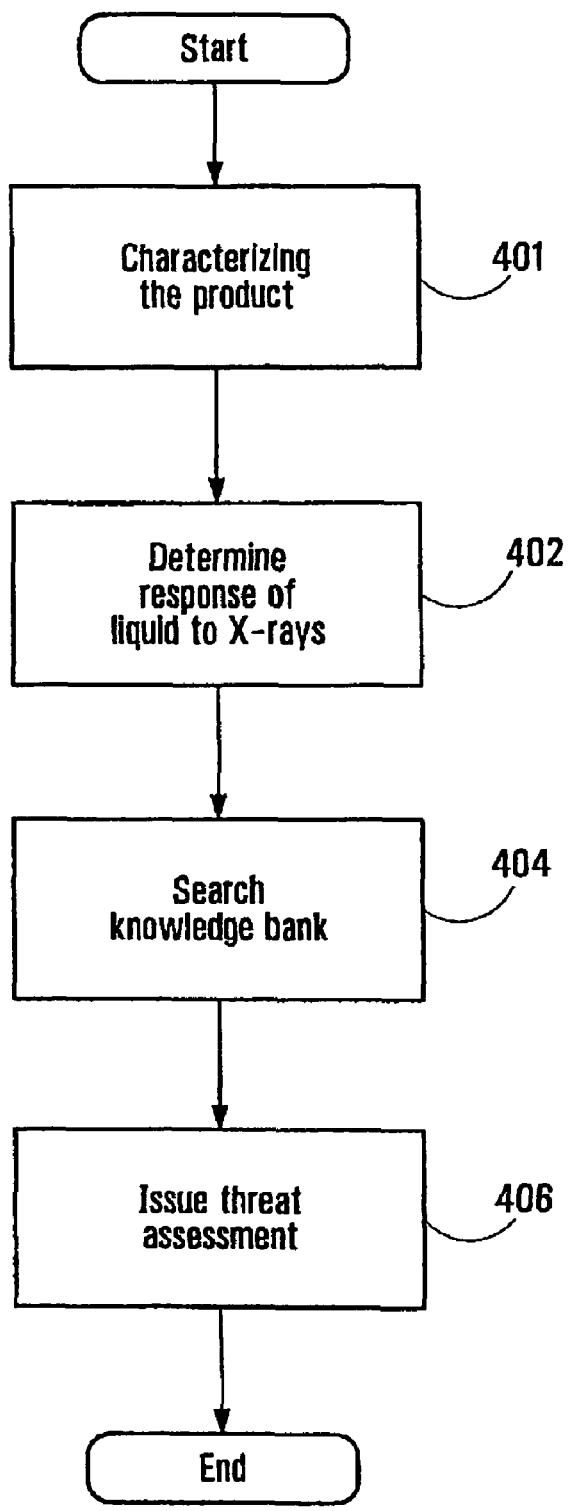
FIG. 2b is a generalized block diagram of the process implemented by the apparatus at FIG. 1 to perform the security screening.

FIG. 2b is a high level block diagram that illustrates the functions performed by the processing module 200 in assessing whether or not the liquid in the container presents a security risk. This block diagram applies to the example of implementation shown at FIG. 1a and also to other examples of implementation that will be described later. The first step of the process, illustrated at 400 is to perform a characterization of the product that is being screened. By "product" is meant the combination container and liquid inside. The characterization step returns information conveying distinctive features of the product that allows distinguishing the product from other products. The characterization step is performed on the container but it may also include the liquid inside. For instance the characterization step 401 may return information such as the general shape of the container, its height, cross-sectional profile and width among many other parameters. Characterization of the liquid is optional and may provide information such as the color of the liquid (assuming of course the container is transparent).

The characterization step 401 can be performed by using different types of equipment capable to capture the distinctive features of the product. One example is an apparatus using penetrating radiation such as the X-ray imaging system 100 of FIG. 1a. This is convenient since the same apparatus can be used to characterize the product and also obtain the response of the liquid in the container to X-rays. Yet another example is to use a device that will obtain an image of the product and perform the characterization based on that image. The image may be two dimensional or three dimensional. Yet another possibility is to use equipment to read machine readable labels or tags on the container. The reading can be done optically or via radio frequency (RF) information capture.

The characterization step of the product is followed by a determination of the response of the liquid in the container to X-rays, as shown at step 402. The response represents the interaction of the liquid with the X-rays as discussed above. The response can be expressed in terms parameters characterizing the liquid. Examples of parameters include:

The density of the liquid;
The effective atomic number of the liquid ($Z_{eff}$);
The diffraction/scattering signature
The viscosity of the liquid At step 404, a knowledge bank is searched on the basis of the product characterization performed at step 401. In the vast majority of cases, the screening process described in FIG. 2b will be performed on commercially available products such as water bottles, juices, soft drinks, personal hygiene items such as toothpaste, shampoo, lotions, etc. The knowledge bank contains characterization data for a number of those commercially available products and the associated responses to X-rays of the genuine liquids in the containers. So, step 404 searches the knowledge bank to locate one or more entries that match the product characterization derived at step 401. If one or more entries are found that match the product characterization, the corresponding responses to X-rays are extracted from the knowledge bank and compared to the response obtained at step 402. If the response extracted from the knowledge bank 400 matches the response obtained at step 402 then the process concludes that the product that is being screened is a genuine product, in other words the liquid inside matches the commercial identification on the container. On the other hand, if no match is found, such as when the response to X-rays derived at step 402 does not match any of the responses associated with the one or more entries extracted from the knowledge bank 400, this constitutes a good indication that the original liquid in the container has been substituted with a different liquid.

The process determines at step 406 a threat assessment on the basis of the knowledge bank search. The threat assessment conveys information indicating if the product is a security risk. Any container that holds' liquid which is other than the commercial labelling on the container is considered suspect. Although there may be perfectly legitimate cases (a water bottle filled with juice) those instances are still flagged as security threats to provide the security personnel at the check point to investigate further.

Note that the mere fact that a product can be matched to an entry in the knowledge bank 400 does not per se indicate that the product is safe. While the knowledge bank 400 contains a large number of reference information for safe and legitimate products, it may also contain reference entries for prohibited products. If a product can be matched to an entry for a prohibited product then an "unsafe" threat assessment will issue. For instance, if a container labelled as holding acid or another corrosive or flammable substance is scanned, it will be considered as a threat irrespective of the results of the knowledge bank search. If a match is found then it means that the liquid in the container has not been substituted with something else but since the liquid is prohibited then the assessment triggers a security alert. On the other hand, if no match can be established then the product is considered suspect because the original liquid may have been substituted with something else.

In the above examples, the knowledge bank 400 provides a threat status reference. If a match is found with an entry in the knowledge bank 400, then the threat status of the product can be derived on the basis of the threat status of the entry. In a possible variant, the knowledge bank 400 is designed in a way as to provide no threat status information directly or indirectly on the entries it contains. In this instance, when a match between a product that is being scanned and an entry in the knowledge bank 400 would, therefore, indicate that the response of the liquid in the container, as determined by the processing module 200 is essentially correct. Those correct measurements therefore can be used as a sound basis for further processing or assessment to derive the threat status of the product. For example, the response of the liquid to x-rays is used to determine the density of the liquid and its effective atomic number. If a match in the knowledge bank 400 has been found, this means that the determined density and effective atomic number values have been validated and can be relied upon to perform the threat status assessment. The actual threat status assessment can be done on the basis of a combination of those values; certain combinations can be associated with dangerous materials while certain others with safe materials.

In the instance where the step 404 fails to find a match between the product and an entry in the knowledge bank 400, the option exists to assume that the product is a security threat since no reference to an entry is possible that has a known security threat status or at least one that can validate the response of the liquid determined by the processing module 200. Another possibility is to continue the processing and rely nevertheless on the response of the liquid as determined by the processing module 200 to provide a threat assessment.

Figure 3:
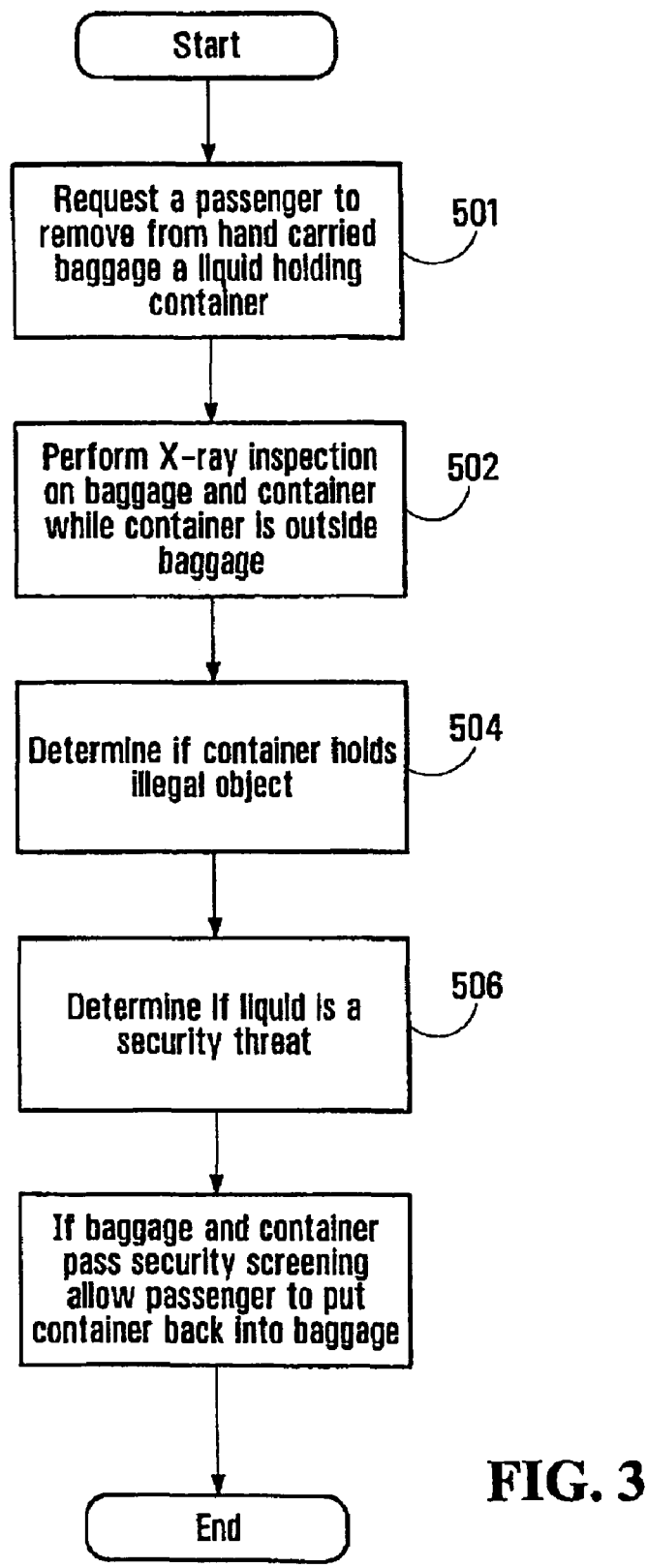
FIG. 3 is a block diagram of the procedure followed by passengers to have their hand carried baggage screened at the security checkpoint.

FIG. 3 is a flowchart of the method that is implemented at a security checkpoint at an airport or any other suitable location to screen hand carried baggage that relies on one example of implementation of the liquid screening process described earlier. The security checkpoint where this method is implemented would use an X-ray imaging system of the type shown in FIG. 1a for example. At step 501 the passenger approaching the checkpoint is requested by security personnel or shown directives appearing on a board or any suitable display to remove any containers holding liquids that may be present in the hand carried baggage. At step 502 the containers are placed in a tray and put on the conveyor belt of the X-ray imaging system. The hand carried baggage is similarly put on the conveyor belt of the X-ray imaging system. The containers and the hand carried baggage are therefore separately scanned but in a serial fashion by the same X-ray imaging system. At step 504 the operator of the X-ray imaging system examines the X-ray image that is generated as a result of the X-ray scan to determine if it contains illegal objects. At step 506 the containers in the tray are scanned and the image signal 116 is processed by the processing station 200 to determine if anyone of the liquids poses a security threat. If no security threat is found then the passenger is permitted to put the containers back in the hand carried baggage and to proceed beyond the checkpoint.

Figure 7:
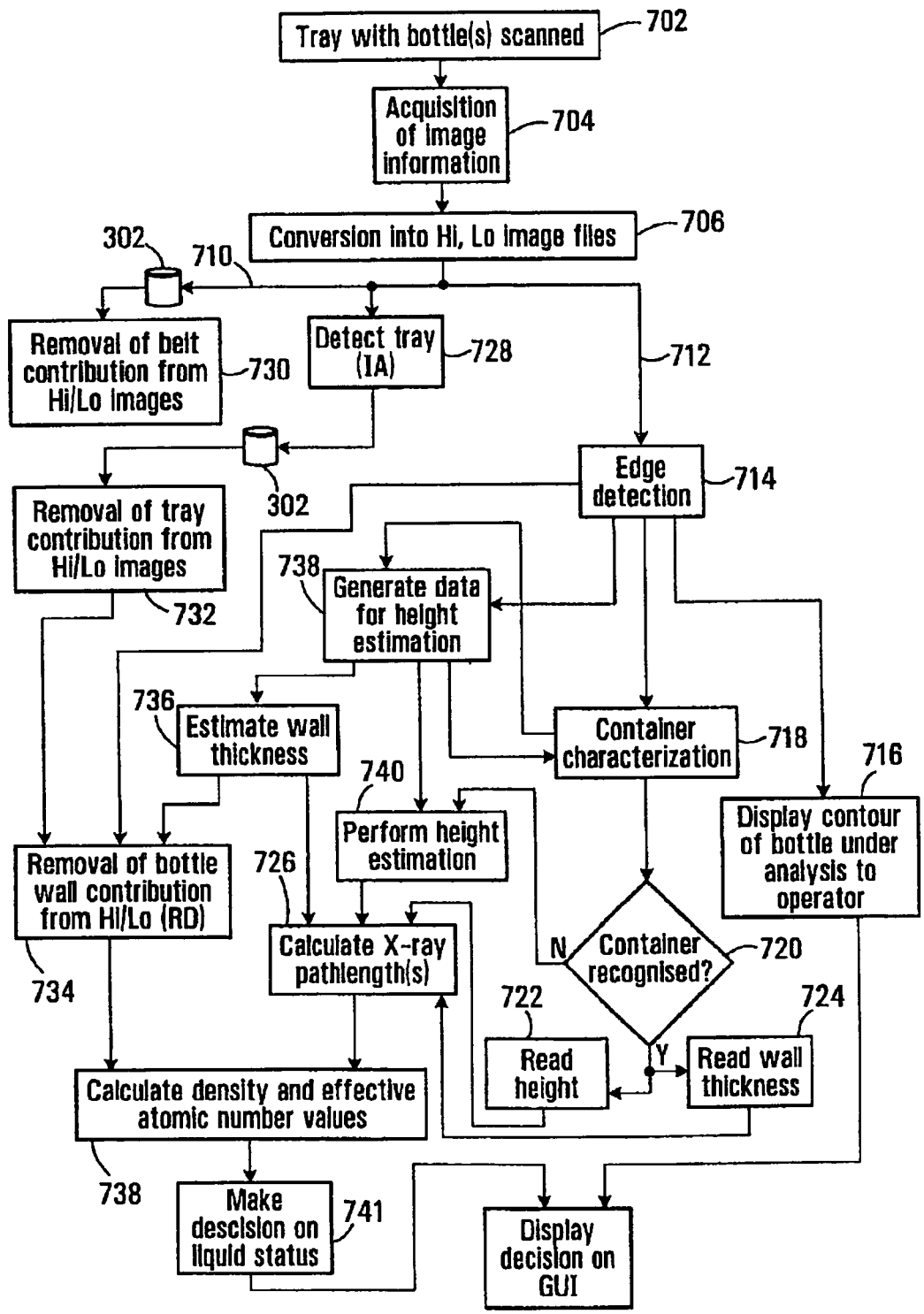
FIG. 7 is detailed block diagram of a first non-limiting example of the process shown in FIG. 3.

FIG. 7 is a more detailed flowchart of the process for performing a security screening on a container holding a liquid, according to a first non-limiting example of implementation. The process uses X-ray scanning to perform the characterization of the product (container+liquid) and also to determine the response of the liquid to X-rays. In other words a single X-ray scan is used to extract both pieces of information. One example of an X-ray imaging system that can be used for this purpose is the equipment manufactured by Gilardoni in Italy, model number FEP ME 640 DETEX. This machine is a dual energy device that produces X-rays at high and low energy values that are HI (high)=74.298 keV and Lo (low)=55.398 keV, respectively.

Figure 8:
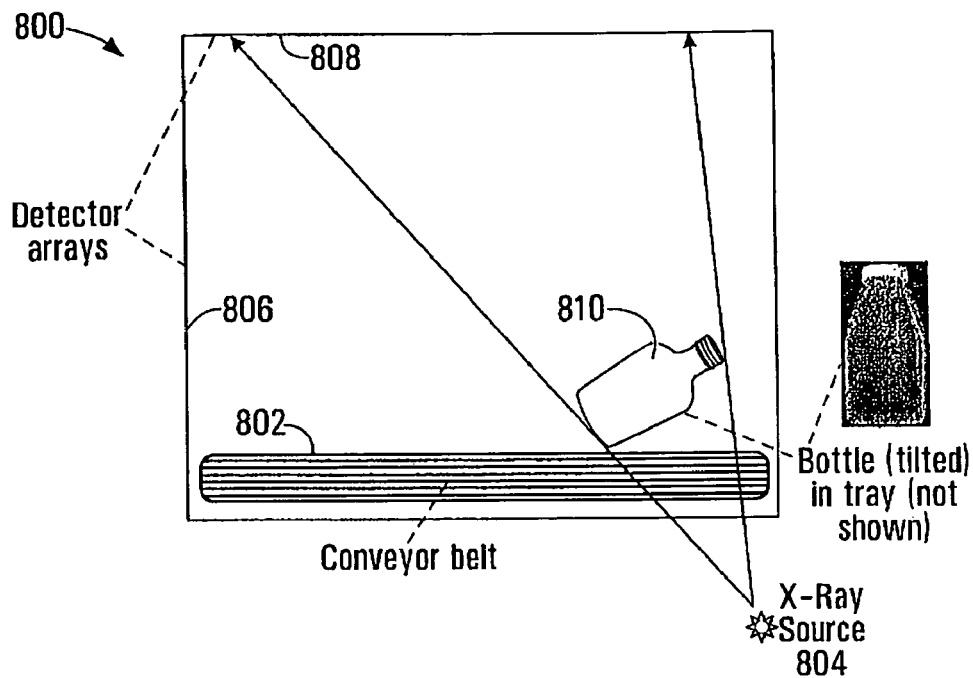
FIG. 8 illustrates an experimental set-up for implementing the method shown in FIG. 7.

FIG. 8 illustrates the general configuration of the X-ray imaging system. The machine 800 has a conveyor belt 802 on which items to be scanned are placed. The X-ray source 804 is located below the conveyor belt 802. Detector arrays 806, 808 are placed on the vertical and the horizontal walls of the casing. For clarity, when the conveyor belt 802 advances the container through the x-ray machine 800, the direction of movement would follow an imaginary line that would be perpendicular to the sheet of the drawing.

A container that is being scanned in shown at 810. In this example, the container is a 1.3 mm thick polypropylene bottle filled with liquid.

Referring back to the flowchart of FIG. 7, the process starts at step 702 where the container is placed in a tray (not shown in FIG. 8 for clarity) and then placed on the conveyor belt 802.

Figure 9:
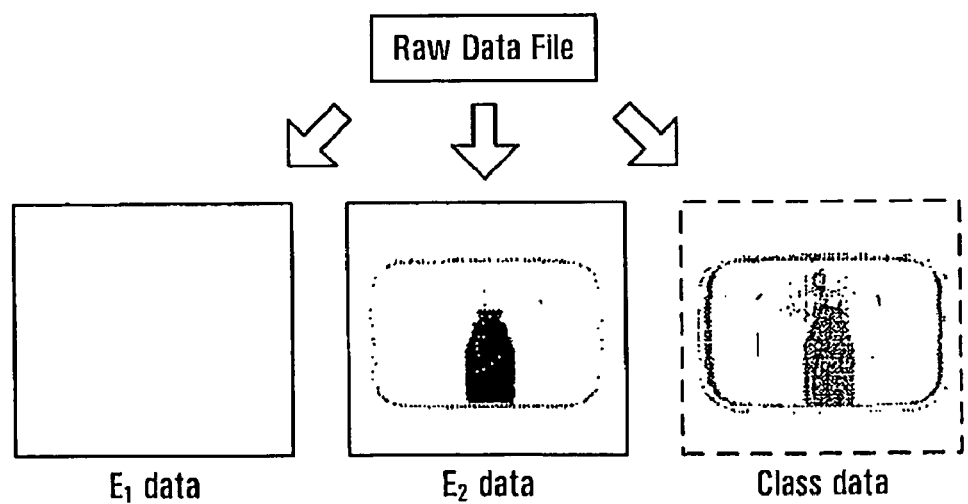
FIG. 9 is an illustration showing the image information derived from the set-up of FIG. 7.

The X-ray scan is then performed. At step 702 the processing module 200 (FIG. 1*a*) acquires the image information 116. In this particular example, the image information 116 is the raw data file output by the X-ray imaging system. The raw data file is then converted at step 706 into distinct image files. This is best shown at FIG. 9. The raw data file exported from the X-ray imaging system is converted into three separate image files, namely HI, Lo and class data. The Hi file represents the X-ray attenuation at the HI energy level. The Lo file represents the X-ray attenuation at the Lo level. Finally, the class data file is the material classification image that uses colors to illustrate the materials from which the objects shown in the image are made. Class data files are generated by the X-ray imaging system directly and they are normally displayed on the monitor of the X-ray imaging system. In this particular example the class data information is not being used, however one can certainly envisage integrating the class data information to the processing to further refine the results of the security assessment.

The HI and the Lo files are grey level image files showing X-ray energies quantified in a number of different levels. The number of grey levels used can vary depending upon the desired resolution; usually the higher the number of grey levels used the better the precision will be. Test conducted with images encoded at 256 grey levels (each pixel is represented by an 8 bit value) have demonstrated that the process works, however the error resulting from the loss of information due to the fairly coarse encoding is not negligible. Therefore, grey levels in excess of 256 would be preferred. However, images encoded at less than 256 grey levels can still be uses for some specific applications that require a lesser degree of detection detail.

Referring back to FIG. 7, the image files HI and Lo are then subjected to two parallel processing threads, 710 and 712 that determine respectively, the density and effective atomic number of the liquid and characterize the product. Note that these threads are not independent. The results of the processing thread 712 are supplied to the processing thread 710, such that the density and effective number computations can take into account the X-rays attenuation resulting from the presence of the container.

Figure 10:
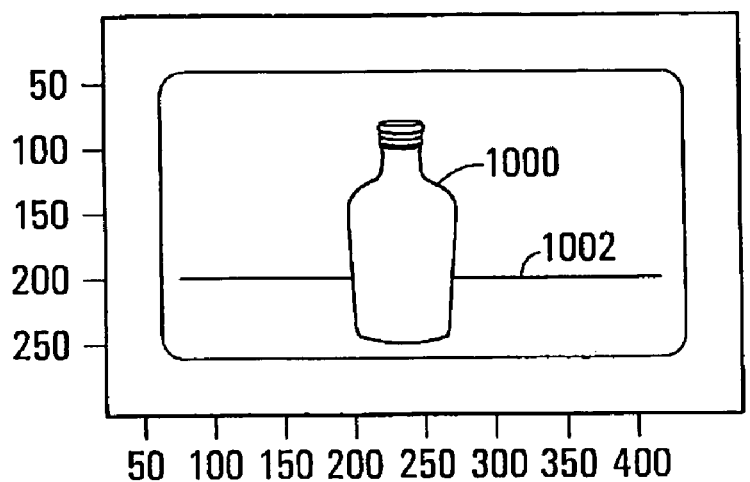
FIG. 10 is an X-ray image of a container holding a liquid, showing a line-like Region Of interest (ROI) along which grey level values are calculated.
Figure 11:
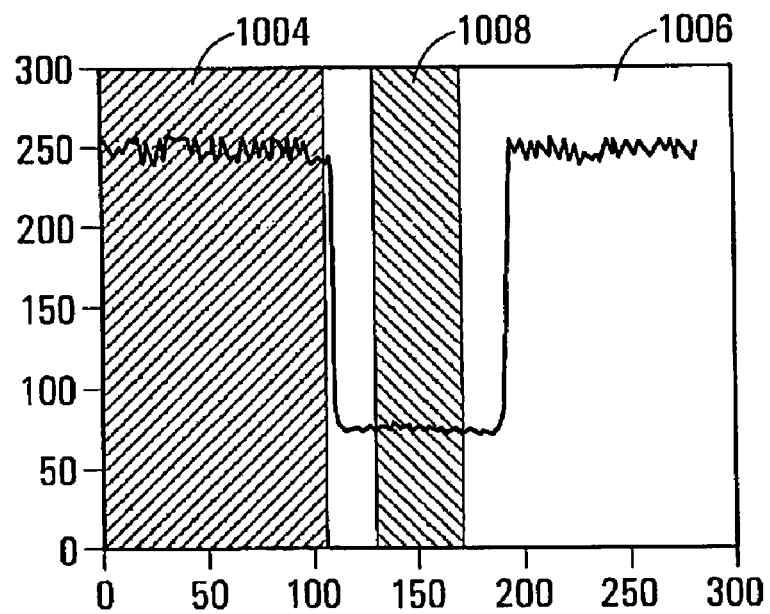
FIG. 11 is a graph illustrating the grey level profile along the ROI of FIG. 10.
Figure 12:
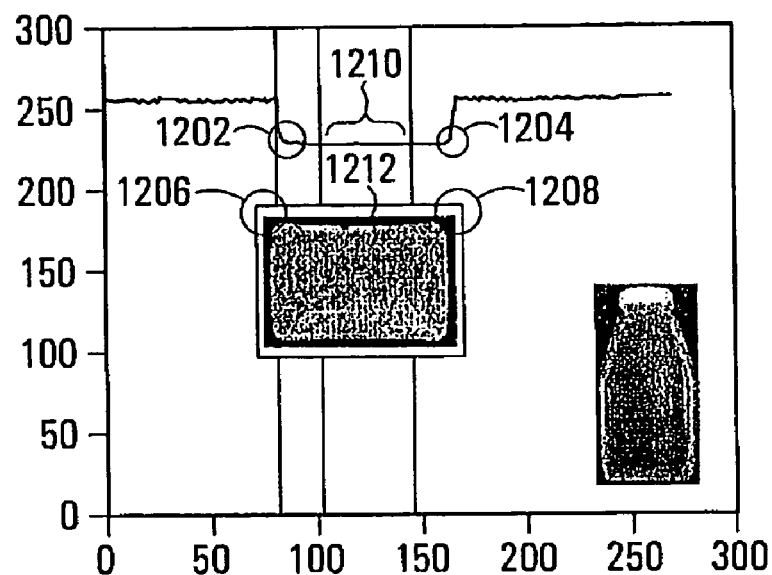
FIG. 12 is a graph illustrating the grey level profile of a high energy (hi-E) X-ray image of a container holding a liquid, showing that the grey level profile matches the cross-sectional shape of the container.
Figure 13:
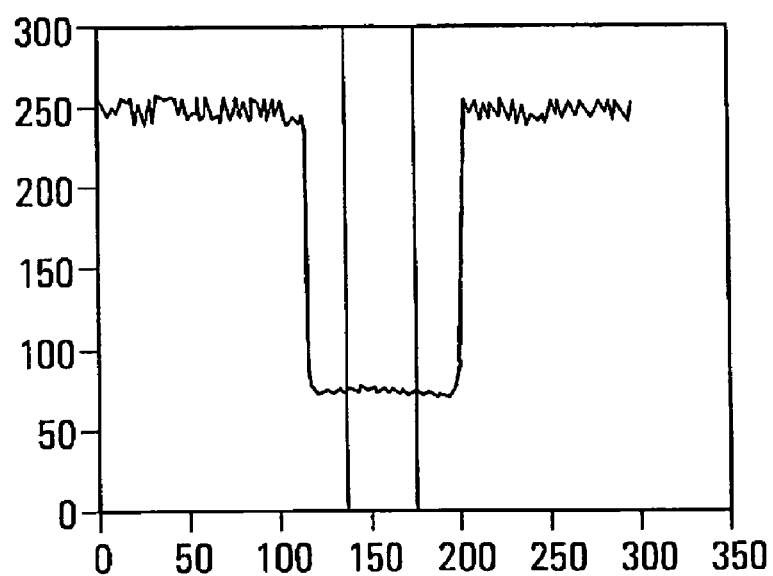
FIG. 13 is a graph illustrating the grey level profile of the low energy (low-E) X-ray image of the container shown in FIG. 12, also showing that the low-E grey level profile matches the cross-sectional shape of the container.

The processing thread 712 starts at step 714 where an edge detection of the container is performed. The purpose is to derive from the information in the HI, Lo image files the location and characteristics of the container. FIGS. 10 and 11 illustrate the general principle of the edge detection process. Consider in FIG. 10 the X-ray image of the container 1000 (Lo image information). FIG. 11 shows the grey level profile in the image taken along the imaginary line 1002 drawn across the container 1000. The areas 1004 and 1006 in FIG. 11 correspond to areas along the line 1002 that are outside the container 1000. The zone 1008 corresponds to the location of the container. It can be observed that the shape of the grey level profile curve matches quite precisely the cross-sectional shape of the container 1000. FIGS. 12 to 18 provide additional examples. FIG. 12 is the HI image of a container and the associated grey level profile curve. FIG. 13 shows the grey level curve of the corresponding HI image. In both cases, the curves match the generally rectangular cross-sectional profile of the container. Specifically, the inflection points 1202 and 1204 correspond to the container edges 1206 and 1208, respectively. The flat region 1210 between the inflection points 1202 and 1204 corresponds to the flat top surface 1212 of the container.

Figure 14:
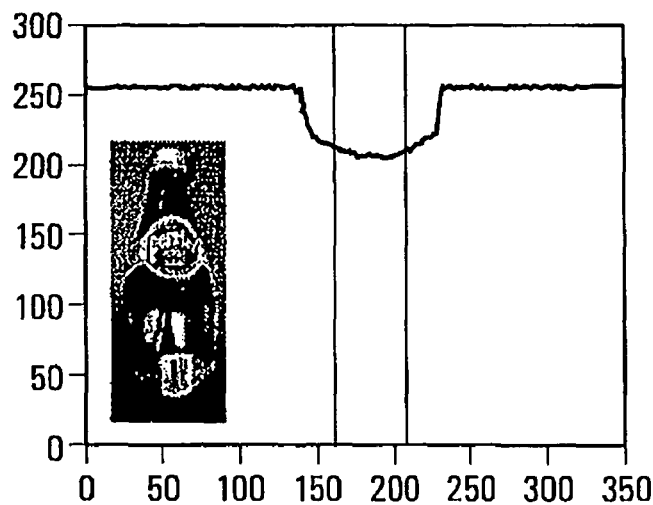
FIGS. 14 to 18 are graphs illustrating the grey level profiles of hi-E X-ray images of different liquid containers and the corresponding container shapes.
Figure 15:
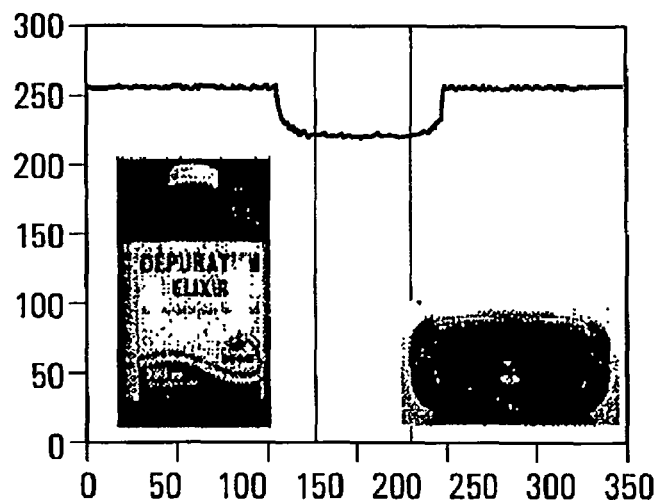
Figure 16:
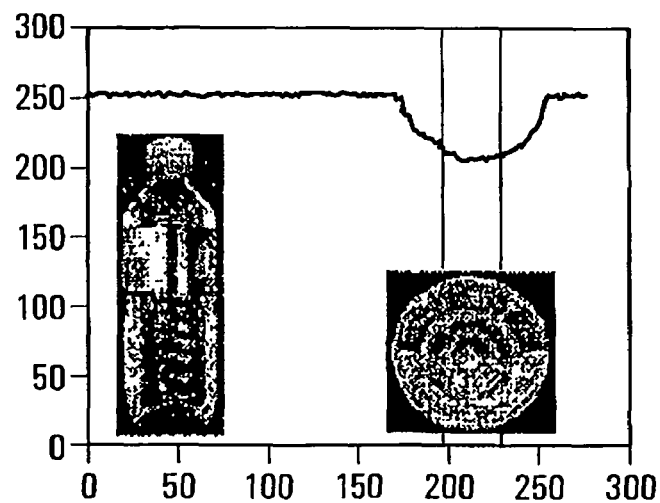
Figure 17:
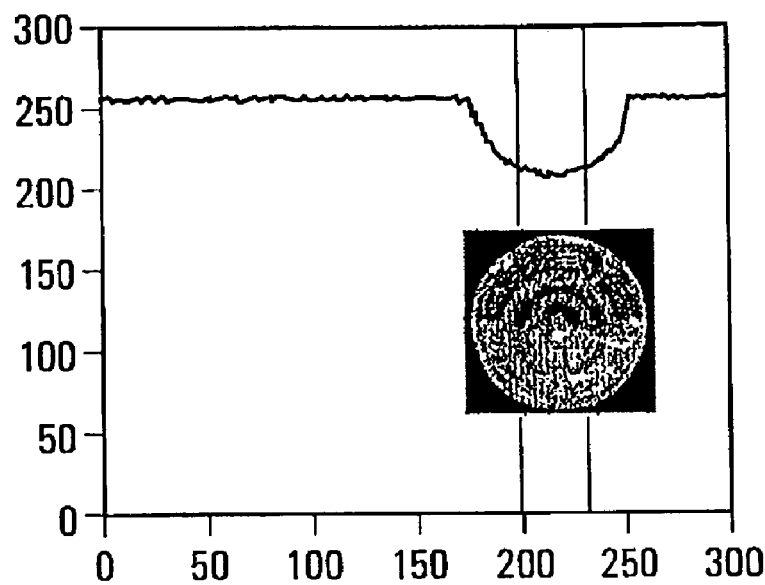

FIGS. 14, 15, 16 and 17 show examples of grey level profiles of containers having rounded features. FIGS. 14, 16 and 17 clearly show that the grey scale profile matches the rounded cross-sectional contour of the bottle.

Figure 18:
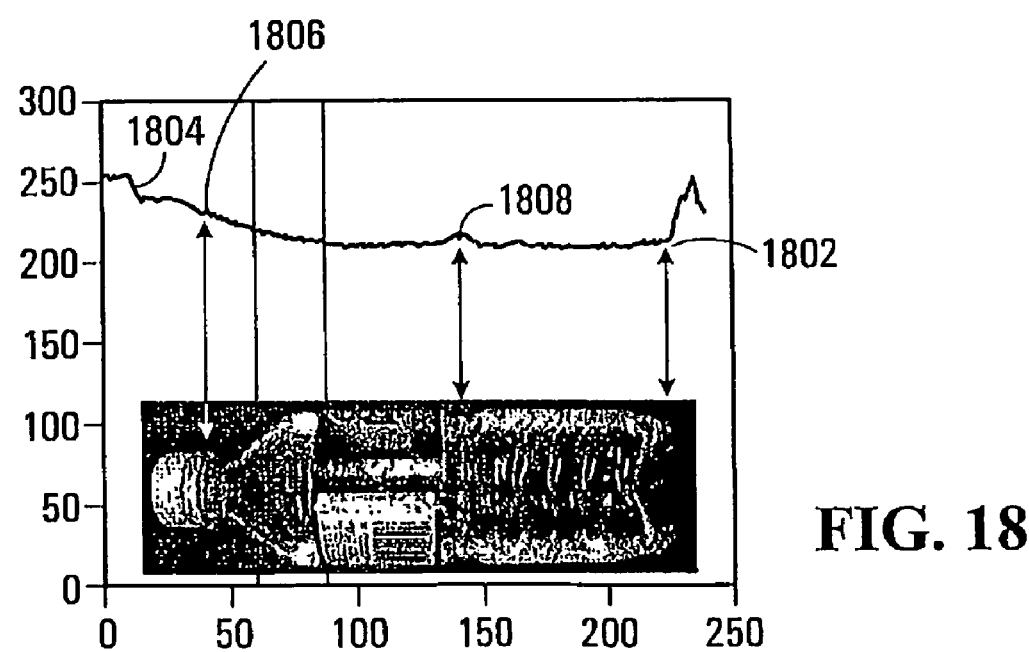

FIG. 18 is the grey level profile along the container (from top to bottom). Again the profile shows characteristic features of the container. In particular, the area 1802 of the curve corresponds to the bottom portion of the container, the area 1804 shows the top of the container, the area 1806 reveals the notch below the cap and the depression 1808 corresponds to the waist in the middle of the container.

Figure 30:
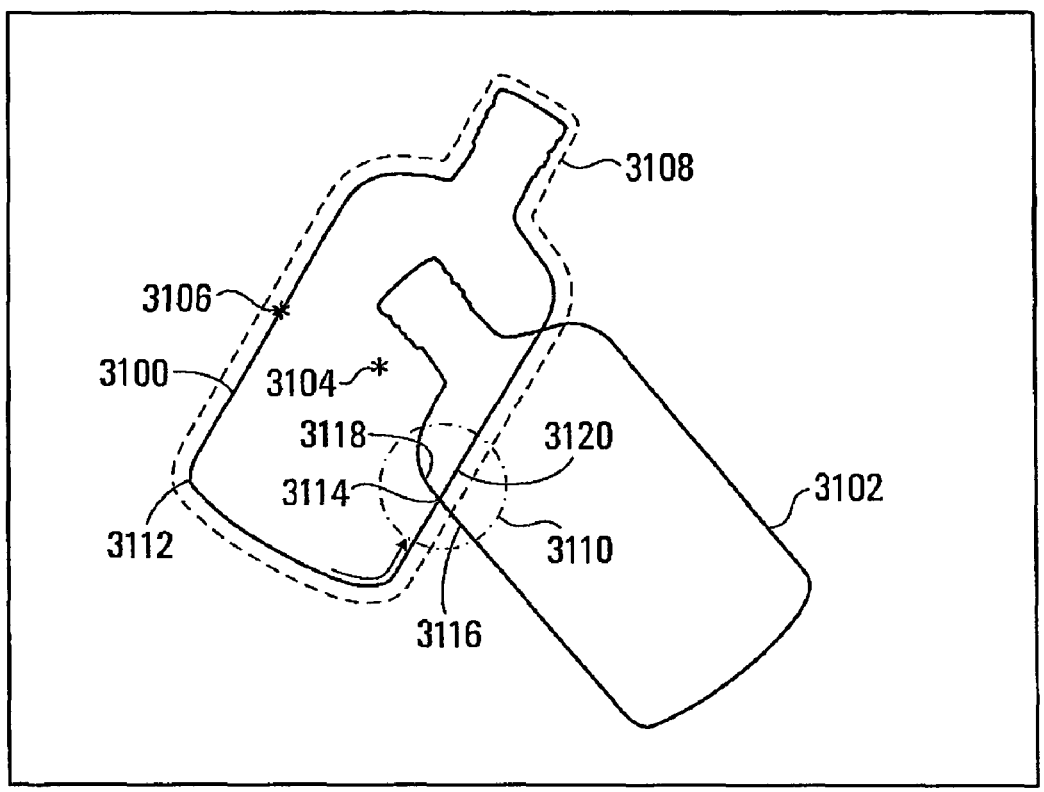
FIG. 30 is a simulated x-ray image of two overlapping containers.

Referring back to FIG. 7, the edge detection process 714, therefore performs an analysis of the HI and the Lo image data to detect the edges of the container. Assume for the sake of this example that the container lies horizontally in the tray as it is being scanned by the x-ray machine. Accordingly, the grey level image produced by the x-ray machine will resemble a plan view of the container. The software executed by the processing module 200 which performs the edge detection process applies the following logic:

1. The first step is to locate a portion of the edge. The software searches for detectable grey level transition that occurs in the image as a result of the container wall. Specifically, due to the structure/material of the container wall a well defined grey level transition will show in the image. To facilitate the edge detection process it is possible to provide the operator console 350 with user interface tools that will allow the operator to designate in the X-ray image the general area where the container is located. In this fashion, the software will start the image analysis in an area of the image that is known to contain the image of a container. Specifically, the user interface on the console 350 is designed such as to display to the operator 130 the X-ray image obtained as a result of the scanning operation. The X-ray image displayed may be the derived from the HI image data, the Lo image data or a combination thereof. Once the image is shown to the operator 130, he or she uses a tool to indicate where a container lies. FIG. 30 shows an example of such x-ray image where several containers appear at once. Specifically this image shows two containers 3100 and 3102 that are partially on top of each other. This may arise when they have been placed in the tray hastily, which is likely to occur in practice quite often.

The operator 130 first identifies the container to be processed. Assume that this is container 3100. The operator 130 then uses a user interface tool to designate the container 3100 to the software. The tool may be any suitable user interface tool such as pointer device such as a mouse or a touch sensitive feature allowing the operator 130 to touch the screen at the area of interest. When the pointer device is activated at the location 3104, which by convention is deemed to correspond generally to the centre of the container 3100, the activation will produce location data. The location data identifies an area in the image where the container 3100 resides. The software uses the location data to select the portion of the image data to which the location data points to and starts the image analysis in that area. The selected area corresponds to the location 3104. The software operates with the assumption that the container features that will be identified should have some degree of symmetry about that location. The software scans the image data by moving further away from the location 3104 until a sharp grey level gradient is located that corresponds to a container edge. In principle since the location 3104 is in the centre of the container then a container edge should be detected in the image at two places equally spaced from the location 3104.

Another possibility is for the operator to designate with the pointing device specifically the edge of the container that is to be analysed. For instance the operator 130 "clicks" the mouse or touches the screen with his/her finger at the location 3106 that corresponds to the edge of the container 3100.

Yet another possibility is for the operator to perform the designation by "drawing" on the image a zone curtailing the area where the container 3100 is located. For instance the operator 130 can use the pointing device to draw the line 3108 around the container 3100.

With any one of the methods described earlier, the edge detection software receives operator guidance to perform an image analysis and extract from the image one or more characterizing features of the container 3100.

Figure 31:
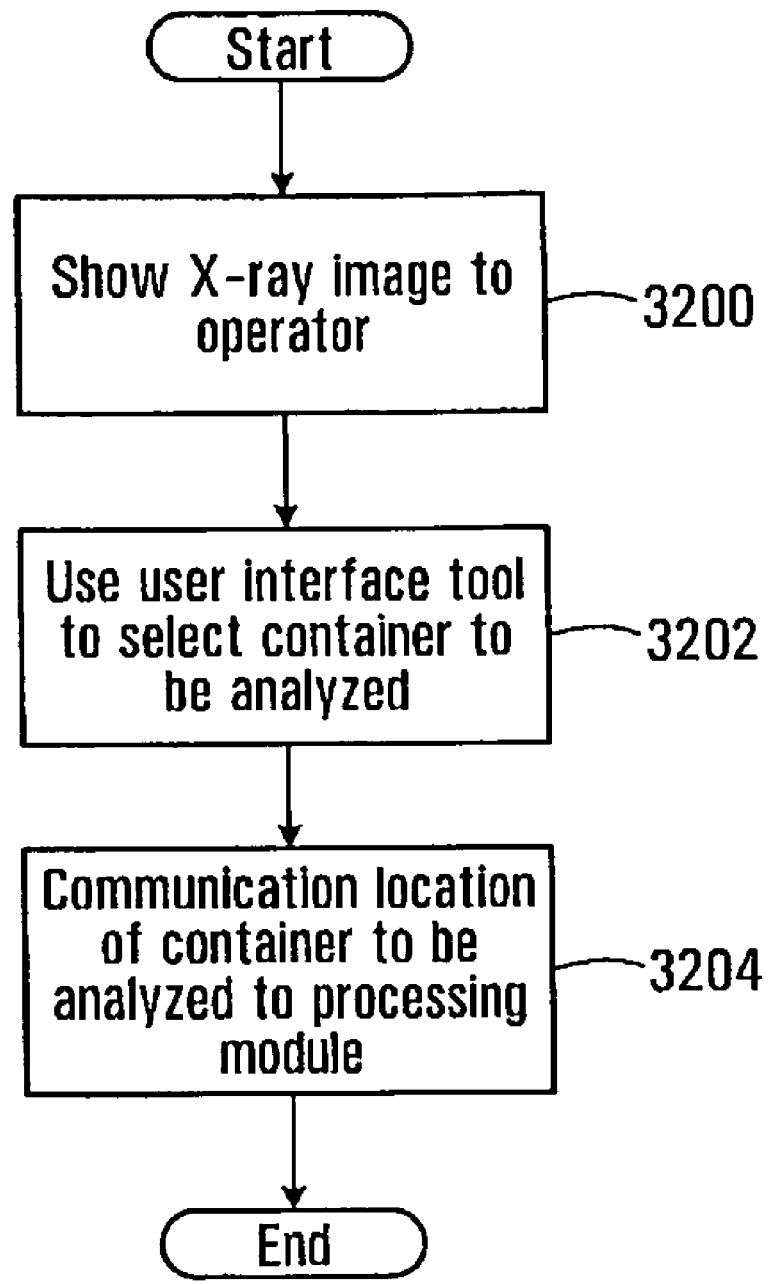
FIG. 31 is a flowchart of a process for allowing the operator to specify on the image at FIG. 30 the container to be analyzed.

FIG. 31 provides a flowchart that that summarizes the above process. At step 3200 the image of the one or more containers is shown on the console 350 of the operator. At step 3202 the operator uses a suitable user interface tool to designate the container to be analyzed. As indicated earlier, the user interface tool may be a pointing device, among others. At step 3204 information about the location in the image where the container is located is communicated to the processing module 200 such that the container analysis can be performed 2. Referring back to FIG. 30, the next step of the process is to track the outline of the container 3100. As the software has identified a portion of the containers edge, the software logic then starts tracking that edge. The tracking logic tracks the sharp gray level gradient in the image to follow the container edge. In doing so, the tracking logic uses a set of assumptions; otherwise it may stray, in particular at areas where two or more container edges meet. This is shown in the area 3110 where the edges of the two different containers 3100 and 3102 intersect each other. If the tracking software is moving along the edge 3112 (in the direction shown by the arrow) it will eventually encounter the location 3114 where the edges of the two containers 3100 and 3102 cross each other. At that location, the edge tracking software has at least three different edges that it can track, namely edge portion 3116, 3118 and 3120, while only one solution (edge 3120 is valid). To avoid straying along the non-valid solutions (edges 3118 and 3116) one of the assumptions is that the edge of the container has no sharp edges or turns. A sharp edge or turn is defined by a radius value, which is a parameter that can be permanently-set or made adjustable. Accordingly, when the tracking software reaches the location 3114 the solutions that correspond to edge portions 3118 and 3116 are rejected because they involve a sharp departure from the existing course (edge portion 3112). Then only solution 3120 remains as valid.

Other assumptions can also be used. One is the container symmetry attribute. Most of the containers are symmetrical about one or more axes. When one side of the container wall has been tracked the other side should in principle be a mirror image of the first side, accordingly only solutions that correspond to that mirror image path would be retained. Another assumption is the maximal or minimal dimension of the container or of its constituent parts. For instance, it is known that containers typically have dimensions that do not exceed a certain limit that is considered to be a maximal value. Accordingly if an edge length extends beyond those limits the detection process may be considered invalid. Similarly, minimal dimensions can also be taken into consideration. If an edge length is below a value that is considered to be a minimum for a container height or width, the detection process may be considered invalid.

3. When the tracking logic has completed the identification of the container edge, then the software performs a validation on the basis of the overall container shape defined. Specifically the software will compute certain geometric features or properties of the container and determine if they fall into acceptable acceptance windows. Examples of such geometric features include:

The height of the container. Usually, most containers would have a height that would fall in a certain range, say from 3 inches up to 18 inches. Any container height dimension outside that range should be suspect.

The width of the container. As in the case with the container height, the container width usually falls in a certain range, for instance between 1 inch and 6 inches. Containers having a width outside that range would also be suspect.

The ratio height/width which is considered to be valid only if the value computed falls in a predetermined range.

A volume prediction of the container. On the basis of the container outline one can predict what the internal volume could be. While to perform an accurate volume computation the actual thickness ($3^{rd}$ dimension) of the container is required, that dimension can be assumed in order to provide volume estimation. The container thickness would normally be in the range of 1 inch to 6 inches. This allows providing a volume estimation that defines a window allowing rejecting solutions associated with volume values that are outside the window.

4. When the container validation process has been completed, the outline of the container can be emphasised to the operator 130, as a final "sanity check". This step is identified at block 716 of FIG. 7. Specifically, the processing module 200 issues commands to the display such that the display visually enhances a portion of the image where the container is located. This makes the container more visible with relation to other objects in the x-ray image. Examples image enhancements include a. Colouring or otherwise highlighting the areas of the image that correspond to the portions where the edge has been identified;

b. Colouring or otherwise highlighting the container in its entirety;

c. De-emphasising the image except the areas where the container lies. This technique does not change the pixels of the x-ray image in the region of the container but changes all the pixels that surround the container image such as to make the container more visible.

The highlighting process uses the edge detection data obtained by the edge detection software as a result of the x-ray image analysis. The edge detection data defines in the x-ray image the areas where an edge has been identified. The highlighting process then uses this information to manipulate the x-ray image pixels such that the container stands out with relation to its surroundings.

If the edge identification has been done correctly the operator 130 would see the container 3100 highlighted. The operator 130 can then apply human judgment on the results. If the edge tracking operation is correct then the results can be accepted and the processing allowed continuing. Otherwise, if the operator 130 sees on the screen a highlighted shape that does not correspond to a container then he/she aborts the operation.

At step 718 the edge detection data obtained by the edge detection software is processed to extract one or preferably more that one characteristics of the container. Examples of characteristics include:

The height of the container
The maximal transverse dimension of the container;
Wall thickness
Generalized geometric shapes that are found in the container.
  The geometric shape identification is a software processing of the container image to try to identify in that image geometric features or shapes that can be used to characterize the container. For example, the software may look at the main body of the container (disregard the neck portion) to determine if the container falls in any one of a set of predefined geometric shapes. Examples of geometric shapes include:
  rectangular container;
  square container;
  upwardly tapered container;
  downwardly tapered container.

At step 720 the knowledge bank 400 is searched on the basis of the characteristics of the container identified previously. The knowledge bank 400 is designed as a database that has a number of entries, each entry being associated with a product that a passenger is susceptible to carry in his/her baggage at a security checkpoint where the process of FIG. 7 is being implemented. Each entry includes two different classes of information. The first class is characterization information about the product. The characterization information includes one or more features of the container in which the liquid is stored. Examples of features include:

Container height;
Wall thickness;
The transverse dimension of the container;
Geometric shapes found in the container or the set of predefined geometric shapes to which the container belongs;
Generic container templates;
Physical parameters of the container;
Chemical parameters of the container such as the material from which the container is made;
Height off belt;
Path length calculation parameters (see description later for path length calculation);
Contour details.

In addition the characterization information may also include information about the liquid (other than its response to X-rays), such as the color of the liquid, smell or visual texture, among others. Under the current example, the characterization information includes solely information about the container.

The second class includes the responses of liquids (the genuine products) that are sold or commercially made available in the containers having the characteristics stored in the knowledge bank 400. In the specific example of implementation discussed here, the penetration radiation used to obtain a response from the liquid is X-rays, however, other types of electromagnetic radiation can be used without departing from the spirit of the invention. The information stored in the knowledge bank 400 that characterizes the response to the liquid to X-rays includes density and effective atomic numbers for each liquid. This is useful for applications where the X-ray imaging system only provides an image output obtained on the basis of photons that have passed straight through the sample. For X-ray imaging systems where the image output also takes into account scattering/diffraction then the knowledge bank 400 can also include the diffraction/scattering signature of the liquid.

Figure 22:
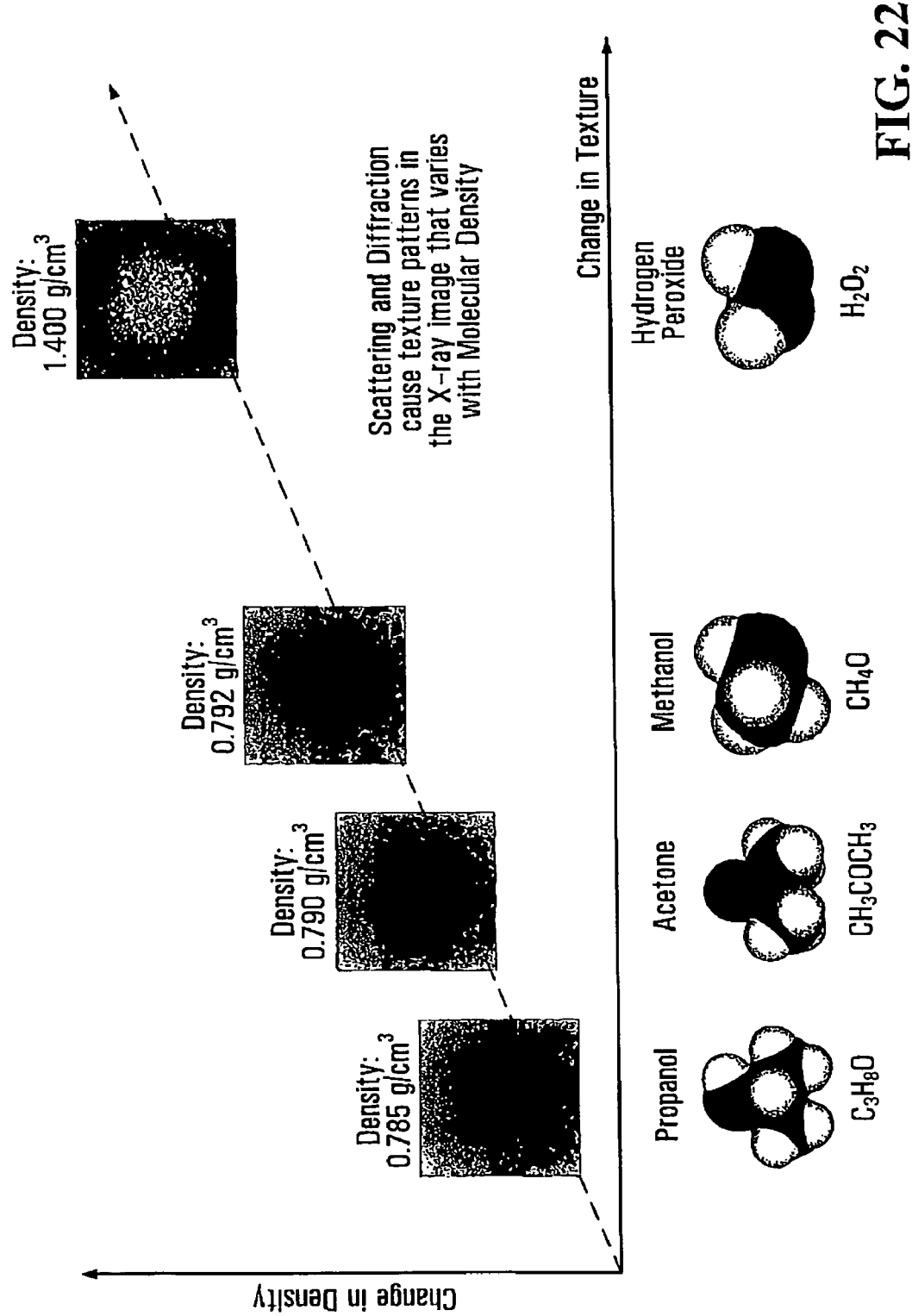
FIG. 22 is a graph showing the variation of the diffraction/scattering signature with molecular density.

FIG. 22 shows a graph of the diffraction/scattering signature for a number of different materials, in particular propanol, acetone, methanol and hydrogen peroxide. The visible texture of the scattering/diffraction signature changes with the density of the materials and constitutes a feature that can distinguish the different materials. In this example, all the materials shown are flammable, hence "illegal" for transport in the hand carried baggage aboard an aircraft.

Accordingly, the knowledge bank can be augmented by storing in association with each entry the diffraction/scattering signature of the liquid. The diffraction/scattering signature can be in the form of an image file or under any other suitable representation that would allow a comparison to be made with the diffraction/signature of a material that is being scanned such as to determine if both signatures match.

The diffraction/scattering signature can be used alone to determine if a liquid matches an entry in the knowledge bank, but preferably it can be used in conjunction with the other elements of information that define the response of the liquid to X-rays, such as density and effective atomic number.

Typically, a neural network would be used to determine if the observed diffraction/scattering signature of a liquid matches anyone of the signatures stored in the knowledge bank 400.

Assuming now that the knowledge bank search is successful and a unique and unmistakable match is found on the basis of the product characterization information provided, then the search will extract the nominal container height (step 722) and the nominal wall thickness (724) of the container from the knowledge bank 400. The read container height and wall thickness are communicated to a processing block 726 which computes the X-ray path length of the container that is being scanned by the X-ray apparatus. This processing block will be discussed in greater detail later.

On the other hand, if no match is found in the knowledge bank 400, then the processing continues at step 740 where a height estimation is performed for the container. In this case, the container height data generated during the container characterization step 718 is read and that information is used as container height information. Similarly, at step 736 an estimate of the container wall thickness is produced from the edge detection data obtained at the edge detection process. Both the estimated edge thickness and container height are then supplied to the block, 726 which performs the X-ray path length computation. The x-ray path length analysis will be described in greater detail later.

The processing thread 710 that runs in parallel with the processing thread 712 performs image processing in order to identify the response of the liquid in the container that is being scanned to X-rays. The first step of the process (step 728) is to locate in the HI and Lo images the tray in which the container is placed for the scanning process. Since the tray signature is known, known image processing techniques can be used to identify the location of the tray in the images and its orientation. The tray signature resides in the memory 302 of the processing module 200.

Figure 24:
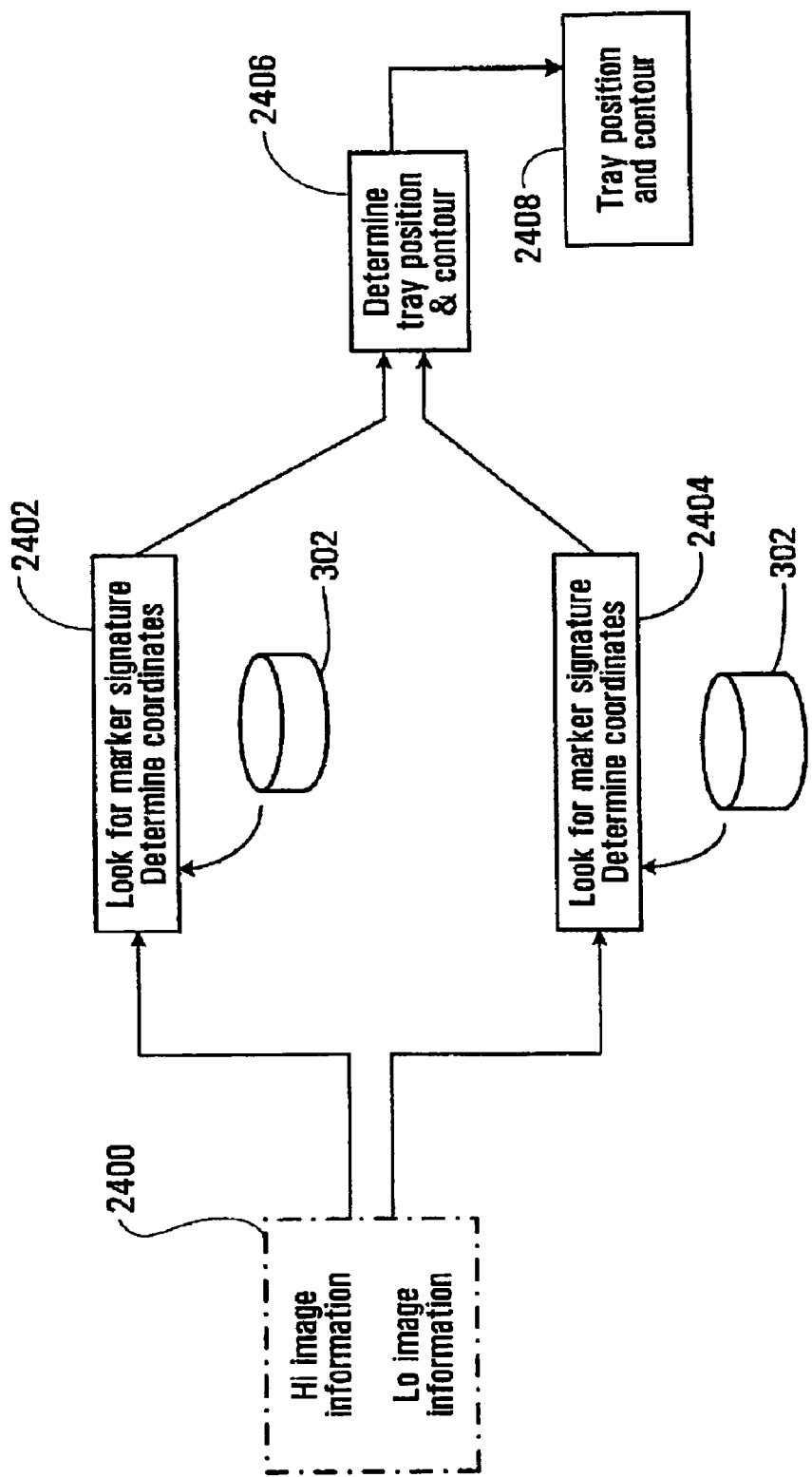
FIG. 24 is a flow chart of a process for performing X-ray image processing to determine in the X-ray image the location and orientation of a tray.

The flowchart of FIG. 24 shows in greater detail the process for identifying the location and the orientation of the tray in the HI and Lo images. To make the identification of the tray simpler, the tray is provided with a marker that is highly visible to X-rays. This may be a piece of metal that will highly attenuate X-rays, which is located at a known position in the tray. Therefore, the detection of the tray position in the image starts by determining where in the HI and the Lo images that marker can be found. For easier identification, the maker can be of an easily recognizable shape unlikely to be confused with other objects placed in the tray during the X-ray scanning process.

At step 2400 the process receives the HI and the Lo image information. The HI image is scanned at 2402 to locate the marker. The image is searched using any well known image scanning techniques on the basis of the marker signature at the HI energy level extracted from the memory 302 of the processing module 200. If the marker is found, its coordinates are recorded. The same process is repeated at step 2404, this time on the Lo image. The coordinates of the marker are also generated.

At step 2406 the tray position and contour is determined by processing both sets of marker coordinates. Since the position of the marker in the tray is known and the shape of the tray is also known, then step 2406 will determine the location of the tray in the HI and Lo images, its contour and its orientation. The process outputs at step 2408 data that defines the location of the tray, its contour and its orientation in both images. The location, contour and orientation should be such as to allow identifying in each image the pixels "overlaid" by the tray, in other words the pixels whose grey levels include the contribution of the tray to the overall X-ray attenuation.

Figure 23:
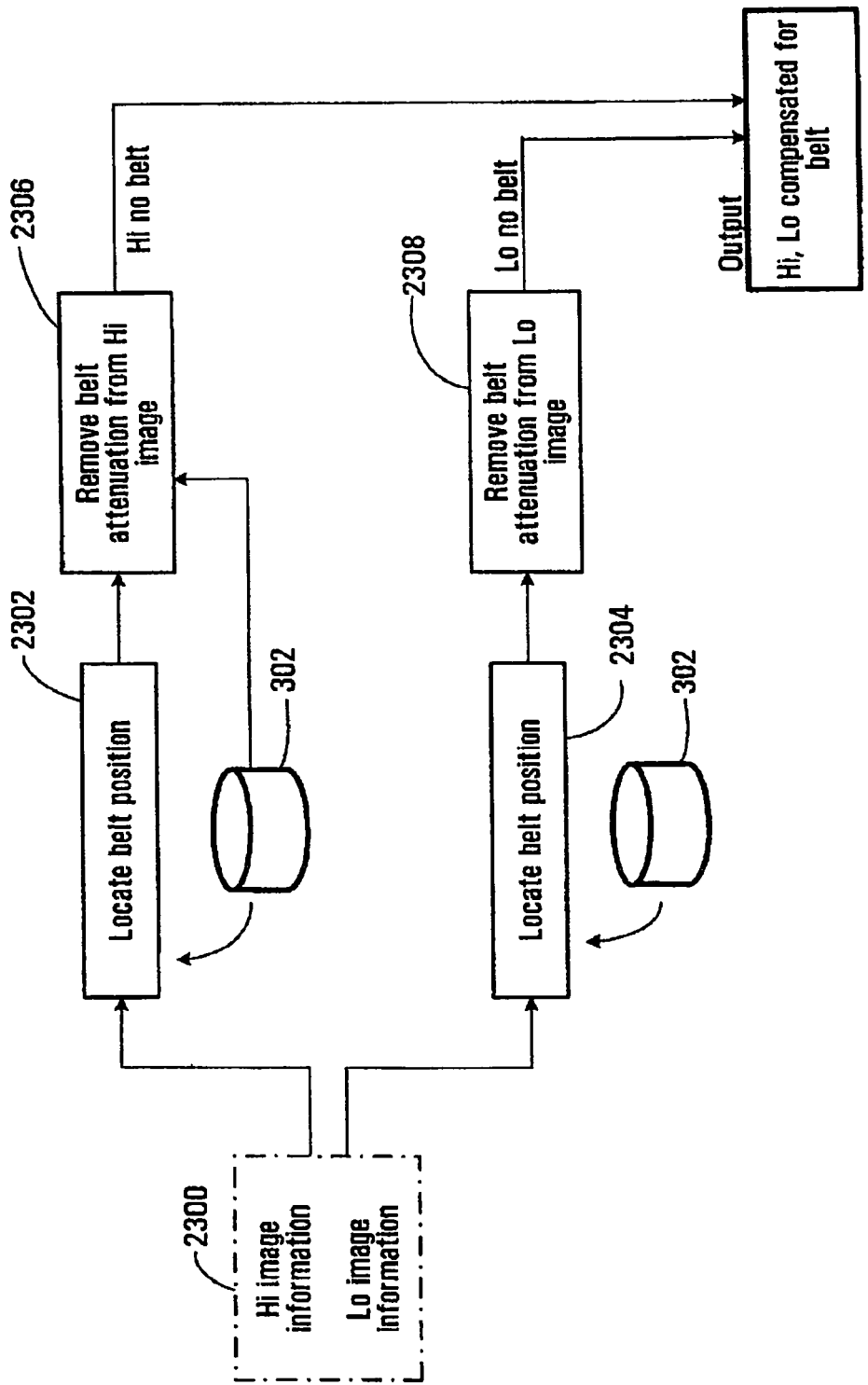
FIG. 23 is a flow chart of a process for performing X-ray image processing to remove the contribution in the image of the belt of the X-ray imaging system.

A somewhat similar operation is performed at step 730 on the HI and Lo images to remove the contribution from the belt 802 (FIG. 8). The belt 802 attenuates to a known degree the X-ray radiation and step 730 compensates the images accordingly. This is done by modifying the grey levels of the pixels in the HI and the Lo images to produce a compensated image that will show a lesser degree of attenuation. The detailed process for removing the contribution of the belt 802 is shown by the flowchart of FIG. 23. Step 2300 receives the HI and the Lo images information. At step 2302 the signature of the belt 802 for the HI energy level is read from the memory 302 of the processing module 200. A search is made in the image such as align or "overlay" the read signature with the signature appearing in the image. A similar operation is performed at step 2304 for the Lo image. Steps 2306 and 2308 compensate the HI and Lo images such as to remove the effect of the belt 802. The compensation is done only in the areas of the HI and Lo images that are encompassed within the belt signature, hence the areas where the gray levels convey attenuation information due to the belt 802 presence (the attenuation due to the belt 802 is stored in the memory 302). The compensation is done by changing the grey levels to remove the attenuation due to the belt. Since the belt 802 is a relatively uniform structure, the compensation that is made on the HI and the Lo images consists of reducing the grey level intensity in each pixel by a value that corresponds to the attenuation caused by the belt 802. Accordingly, steps 2306 and 2308 produce synthetic HI and Lo images in which the effect of the belt 802 is removed.

Figure 25:
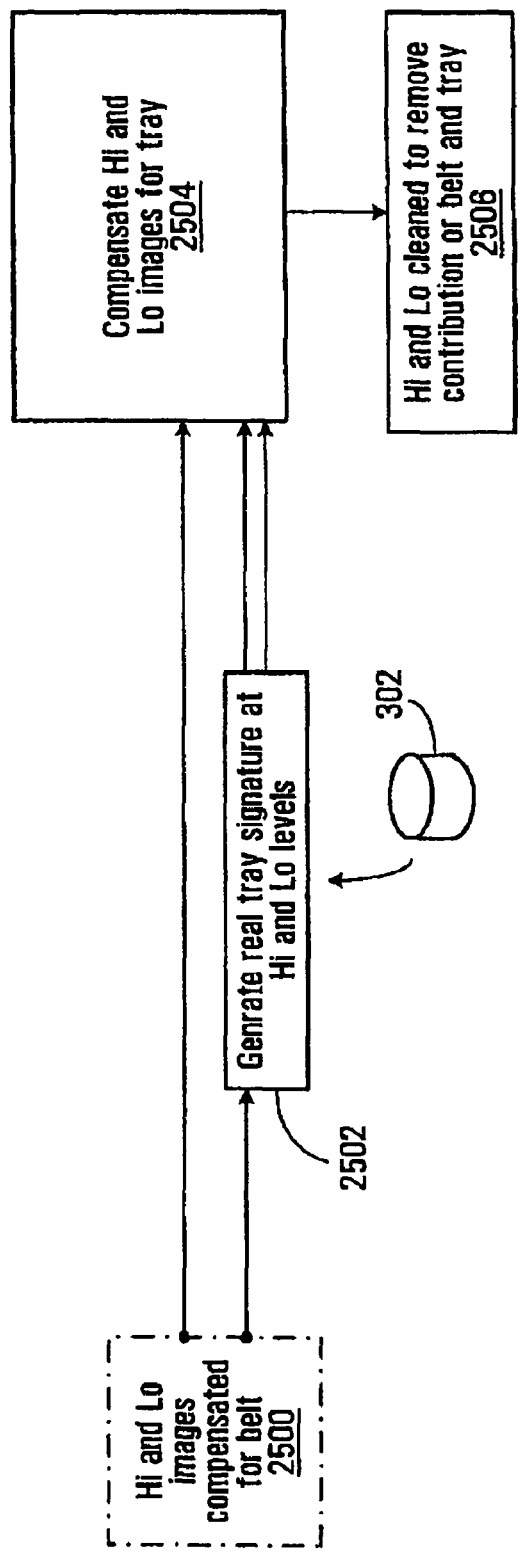
FIG. 25 is a flow chart of a process for performing X-ray image processing to remove the contribution in the image of the tray detected in FIG. 24.

The HI and Lo synthetic images are processed at step 732 (FIG. 7) to remove the contribution of the tray. The details of the tray removal are shown in the flowchart of FIG. 25. The HI and the Lo synthetic images as well as the data that defines the location of the tray (obtained from the process at FIG. 24) are received by the process at step 2500. Step 2502 processes the data that defines the location of the tray for the HI and the Lo levels in conjunction with the tray X-ray signature at the HI and Lo levels. The X-ray signature for the HI and the Lo levels is extracted from the memory 302. The processing at step 2502 modifies the signature extracted from the memory 302 such as to shift it to the current tray location. In other words, the X-ray signature of the tray that is stored in the memory 302 corresponds to a certain reference tray location. To be able to use this signature in cases where the tray is in a position other than the reference position, then the signature must be manipulated such as to displace the grey level features that define the signature to the positions where the tray is actually located. Step 2502 performs this operation by using any suitable image processing techniques that translate and/or rotate the pixels that convey the X-ray attenuation caused by the tray in the actual tray position that was previously determined. This produces a real tray signature, for both HI and Lo energy levels that can be used subsequently to compensate the HI and the Lo images for the presence of the tray.

Step 2504 performs the tray removal operation. The process at step 2504 receives the synthetic HI and Lo images (compensated for the belt) and also the real tray signature generated earlier. The real tray signature for each energy level is "subtracted" from the corresponding synthetic image such as to remove from the synthetic image the X-ray attenuation information resulting from the tray.

Step 2506 outputs the HI and Lo synthetic images that have been cleaned to remove the effects of the belt and the tray.

Referring back to FIG. 7, step 734 further modifies the HI and the Lo Images received from the process at step 732 to remove from the image information the attenuation due to the container wall. The material from which the container is made will determine the extent to which the container wall removal is critical. For glass materials it is necessary to remove their contribution since glass materials tend to attenuate X-ray significantly as in practice they are quite thick. On the other hand, when the container is made of plastic that attenuates X-rays to a much lesser degree, the compensation of the image is not absolutely required. The same also holds true for thin walled metallic containers, such as aluminium beverage cans.

Figure 27:
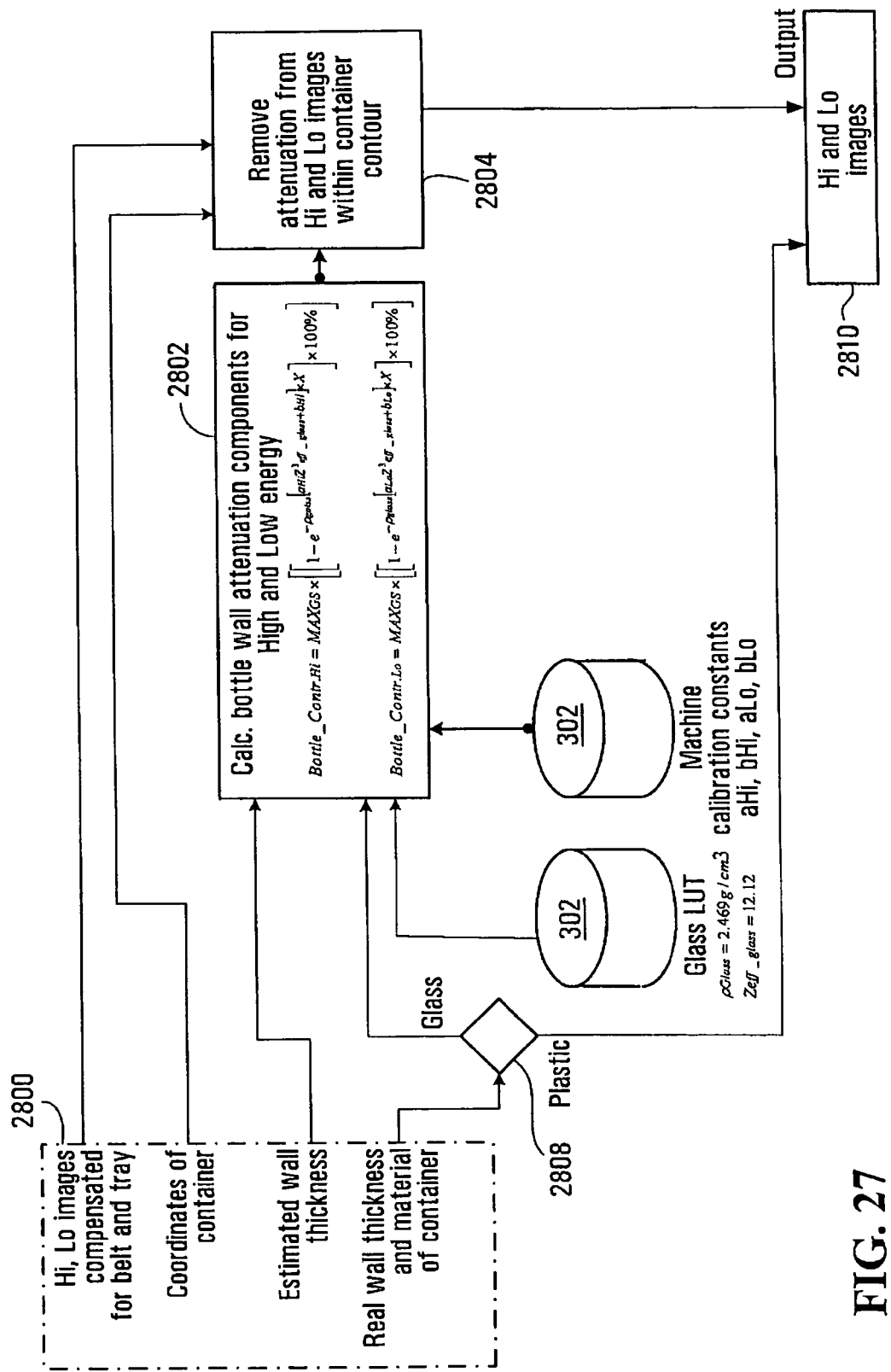
FIG. 27 is a flowchart of a process for performing X-ray image processing to remove the contribution in the image of the wall of a container that appears in the image.

The step 734 receives the HI and the Lo images compensated for the presence of the belt and of the tray, information that approximates the wall thickness of the container (the approximation will be described later), real wall thickness information and material of container extracted from the knowledge bank 400 as output at step 724 (if a match in the knowledge bank 400 has been found) and the coordinates of the container contour from the edge detection process 714. If the product (container+liquid) that is being scanned has been accurately recognized at step 720 (a match exists in the knowledge bank 400), then the approximation of the wall thickness is not required. The wall thickness approximation is used only if the product recognition process at step 720 is uncertain or has failed. The flowchart at FIG. 27 illustrates in greater detail the process for compensating the HI and the Lo images for the attenuation resulting from the container walls.

Step 2800 is the start of the process. That step receives the following information:

1. HI and Lo images compensated for the attenuation by the belt and tray;
2. Coordinates of the container contour. This information is received from the processing at step 714 (edge detection). This information specifies the outline of the container and defines the area of the HI and Lo images that will need to be compensated to remove the effect of the container wall.

3. The estimated wall thickness;
4. The real wall thickness and the material from which the container is made (information obtained from step 724, if available).

If only a wall thickness estimation is available (no real wall thickness information found) then the process proceeds at step 2802 that computes the attenuation brought by the container. Since at that point no knowledge exists about the material from which the container is made, the process at step 2802 assumes that the material is glass, which in most practical cases would be the worst case scenario (the greatest degree of attenuation). The step 2802, therefore computes the attenuation that the glass material of the estimated thickness will create such that the HI and Lo images can be compensated accordingly. The process performed at step 2802 is a computational step that uses the following algorithm for HI energy level image:

$$\text{Bottle\_Contr.Hi} = \text{MAX}_{GS} \lfloor \lfloor 1 - e^{-\rho_{glass}[aHiZ^3_{eff\_glass} + bHi] \times X_1} \rfloor \times 100\% \rfloor$$

and the following algorithm for the Lo energy level image:

$$\text{Bottle\_Contr.Lo} = \text{MAX}_{GS} \lfloor \lfloor 1 - e^{-\rho_{glass}[aLoZ^3_{eff\_glass} + bLo] \times X_1} \rfloor \times 100\% \rfloor$$

Where:
Bottle_Contr.Hi is the container wall attenuation at the HI energy level expressed in percentage;
Bottle_Contr.Lo is the container wall attenuation at the Lo energy level expressed in percentage;
$\text{MAX}_{GS}$ is the Maximum Gray Scale (actual value of the background or input energy)
$\rho_{glass} = 2.469$ g/cm$^3$
$Z_{eff\_glass} = 12.12$
$a_{Hi}$, $b_{Hi}$, $a_{Lo}$ and $b_{Lo}$ are constants that are dependent on the particular X-ray imaging system used for the scanning. The values of those constants are obtained during the calibration phase of the machine and they are stored in the memory 302 of the processing module 200.

The glass density ($\rho_{glass}$) and effective atomic number ($Z_{eff\_glass}$) are stored in the memory 302 of the processing module 200. Alternatively, the glass density and effective atomic number could be stored in the knowledge bank 400, as a parameter of container. In this fashion, it could be possible to provide for each glass container specific density and effective atomic numbers that match well the specific container material. This could be useful if it is expected to find in use different containers made of different glass compositions such that the density and the effective atomic numbers are not all the same across the glass containers population.

Therefore, the step 2802 outputs the attenuation in the X-ray images at the HI and at the Lo energy levels that the glass container produces. The output is supplied to step 2804 that uses this information to compensate the HI and the Lo images accordingly. Step 2804 will be described in greater detail later.

Assuming now that instead of estimated wall thickness information, real wall thickness information is available, then the step 2802 is performed only if the material from which the container is made is glass. Specifically, at decision step 2808 the material from which the container is made is verified. The material from which the container is made is stored in the knowledge bank 400. If the material is glass then step 2802 described above is performed. On the other hand, if the material is plastic then the processing goes directly to the output 2810. In other words, if the container is made of plastic, no image compensation is performed. The reason for bypassing the image compensation is that a plastic introduces a negligible degree of X-ray attenuation, therefore the HI and the Lo images do not need to be compensated.

Step 2804 receives the X-ray attenuation introduced by the glass container for the HI and the Lo energy levels. Also, step 2804 receives the HI and the Lo images compensated for the belt and the tray and the container contour information. Step 2804 performs image processing to remove the attenuation introduced by the container in the area defined by the container contour information. The pixels in the area defined by the container contour information are modified such that their values no longer reflect the contribution of the attenuation introduced by the glass material. Step 2804 therefore outputs at step 2808 HI and Lo images that have been compensated for the influence on the X-rays of the belt, the tray and the container wall. Therefore, the HI and the Lo images now provide attenuation information of the liquid and allow computing parameters of the liquid.

For clarity, it should be mentioned that the compensation for the container wall has essentially the effect to "remove" the container wall in the x-ray image within the contour of the container. In other words the portion of the wall that is generally parallel to the x-ray image plane is being erased. The wall portions of the container that are generally perpendicular to the x-ray image plane and which would define its contour still remain in the image.

Since the HI and Lo X-ray images are two dimensional, the path length calculation, in one non-limiting example of implementation, is an indirect mathematical operation based on a combination of trigonometry operations and shape recognition algorithms. Knowing the exact physical characteristics of the X-ray imaging system, it is possible to calculate the height of the liquid container, and therefore the path lengths followed by the X-ray beams, by using the position of the container on the conveyor belt 802 with respect to the fixed reference points of the X-ray scanner itself. As these reference points remain identical from one scan to the next, the path length calculation is not affected by the random position of the containers in the plastic tray. Should there be bubbles in the liquid under test, their presence can be filtered out by either appropriate filtering algorithms or by considering the bubble physical characteristics in order to remove their contribution from the liquid.

Figure 29:
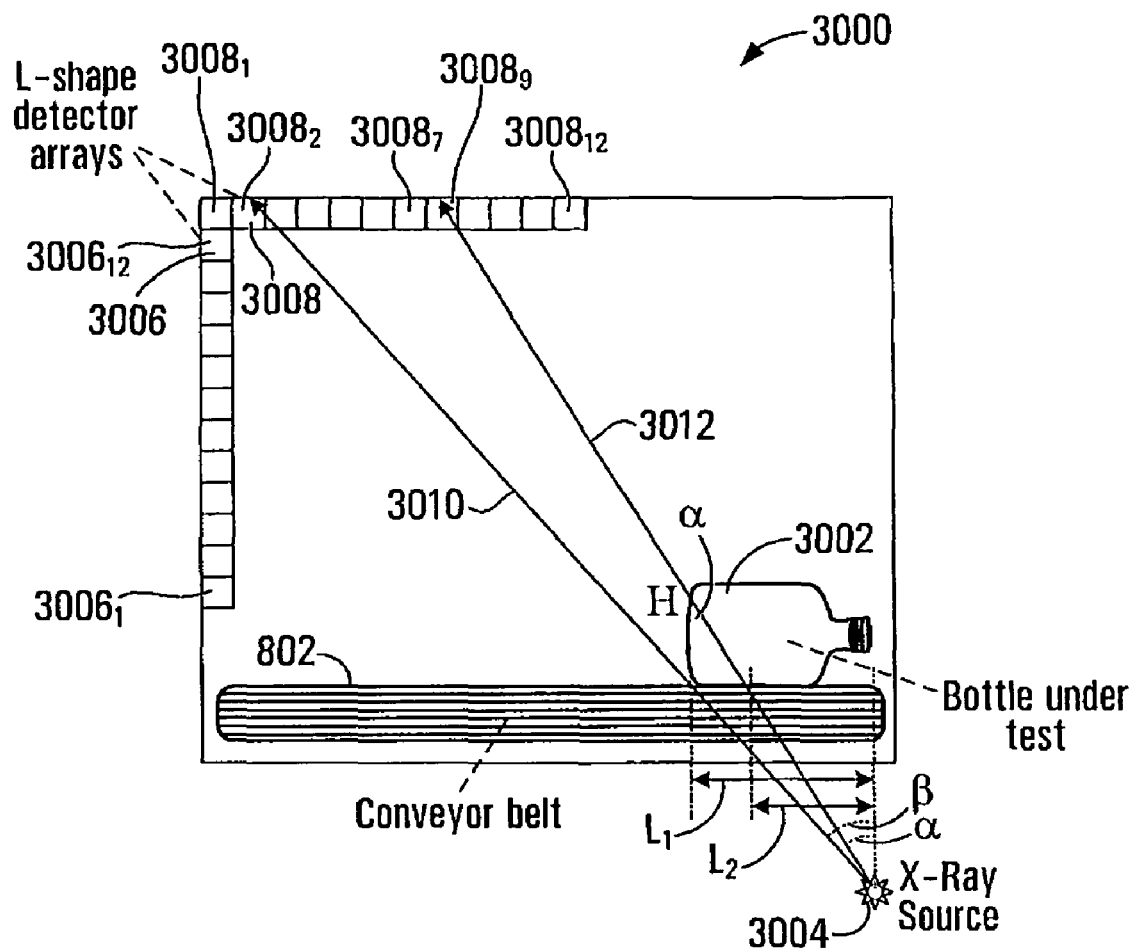
FIG. 29 is a diagram of an X-ray image scanner illustrating a method to compute the path length of the X-ray beams through a body of liquid held inside a container.

FIG. 29 illustrates the path length determination process. FIG. 29 is a cross-section of the X-ray imaging system 3000 showing the belt 802 on which the container 3002 is placed. For clarity, the belt 802 moves the is container 3002 through the x-ray imaging system 3000 in a direction that is perpendicular to the sheet. This X-ray imaging system 3000 has a radiation source 3004 that is located below the belt 802 and also an L-shaped set of detectors that has a vertical array 3006 and a horizontal array 3008. The array 3006 is shown arbitrarily as having 12 detectors, (3006$_1$ . . . 3006$_{12}$) and the array 3008 has 12 detectors (3008$_1$ . . . 3008$_{12}$) as well. Note that in practice, X-ray imaging systems have a much higher numbers of detectors in order to provide a suitable image resolution.

Figure 32:
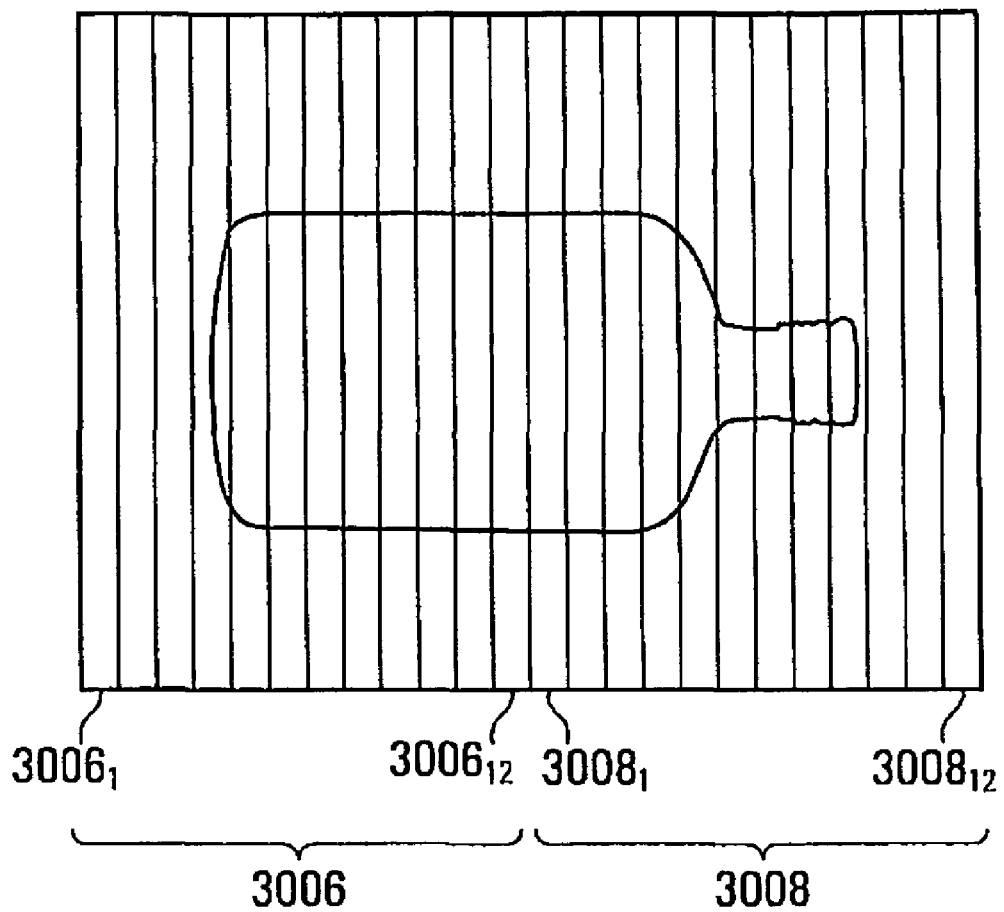
FIG. 32 is a simulated X-ray image illustrating the mapping between image portions and individual detectors of the X-ray imaging system.

The position of the source 3004 is well known and fixed. In addition, the geometry of the detector arrays 3006 and 3008 is such that it is possible to map portions of the x-ray image (Lo and Hi) to individual detectors of the arrays 3006 and 3008. In other words, it is possible to tell for a certain portion of the image, which ones of the detectors produced that portion of the image. FIG. 32 provides more details in this regard. FIG. 32 shows a simulated x-ray image of a body of liquid 3002, shaped in the form of a container. The image is obtained as a result of a movement of the container 3002 by the belt 802 with relation to the detector arrays 3006 and 3008. Therefore, individual detectors of the arrays 3006, 3008 produce individual bands in the image. The image bands are shown in FIG. 32 and for clarity numbered with the corresponding detector reference numerals.

Referring back to FIG. 29 assume for the sake of this example that the X-ray source 3004 is turned on and generates X-ray beams that are directed through the container 3002. While there are many beams passing through the container 3002, consider only two of them, namely the beam 3010 and the beam 3012 that intersect the top and bottom edges of the container 3002. The beam 3010 will reach the detector 30082 while the beam 3012 will reach the detector 30087. By analyzing the image it is possible to determine which detectors of the arrays 3006, 3008 received the beams 3010 and 3012. Specifically, the features of the container 3002 through which the beams 3010 and 3012 pass are first located in the image and their respective positions in the image noted. In particular the processing module processed the x-ray image information to locate the top and the bottom edges of the container 3002 and once those features have been identified, their position in the image is recorded. Since the image positions are mapped to corresponding detectors of the arrays 3006 and 3008, it is possible to derive which ones of the detectors in the arrays 3006, 3008 received the beams 3010 and 3012. On the basis of the position of those features in the image, the detectors are identified. Once the identity of the detectors has bee found, both lengths L1 and L2 can be trigonometrically calculated using angles alpha and beta. Finally, the path length H can be simply derived by the formula H=(L$_1$–L$_2$)tan α. In this example, H would be the height of the body of liquid held in the container.

The above process works well for containers that are generally rectangular in shape. For containers that are rounded, such as cylindrical shapes for instance, the following cylinder parametric equation can be used:

$$\vec{c}(z, \theta) = u(z, \theta)[\cos\theta \hat{\imath} + \sin\theta \hat{\jmath}] + z \cdot \hat{k}$$

Where u(z,θ) will be adjusted according to every individual shape of container.

This equation is a known ray casting formula that is used to calculate object interceptions in 3d space.

Figure 26:
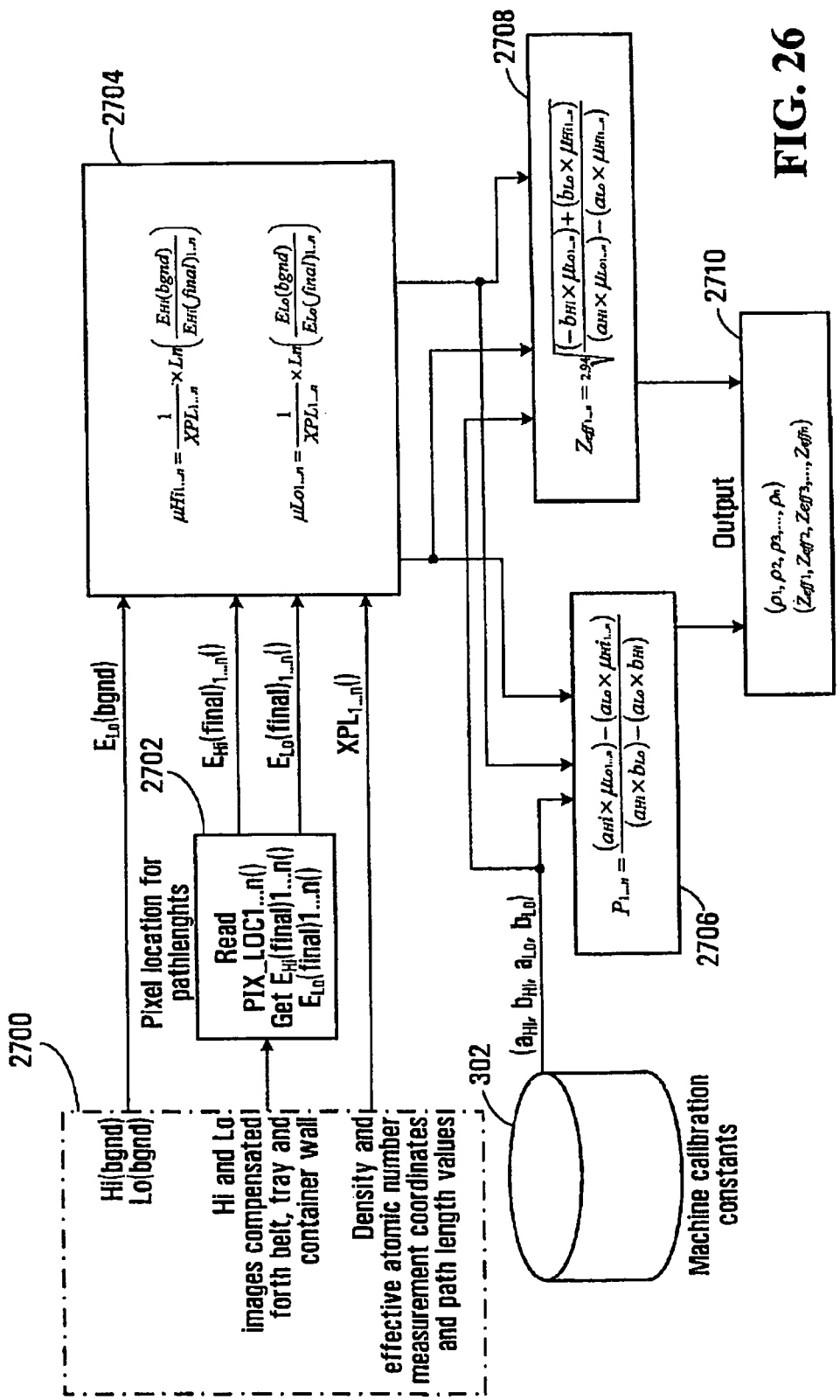
FIG. 26 is a flowchart of a process for performing a calculation of the density and the effective atomic number of a liquid in a X-ray image.

Once the path length through the liquid has been computed at step 726, the process continues at step 738 where the density and the effective atomic number of the liquid are computed. The process will be described in greater detail in conjunction with the flowchart on FIG. 26. The process starts at step 2700. The information that is used to perform the various computations includes:

1. The HI and the Lo images as output from the processing at step 734 (the contribution of the belt, the tray and the container wall have been removed).
2. HI, Lo (bgnd) which are the images compensated for the presence of the belt
3. Coordinates in the HI and the Lo images that are within the boundary of the liquid body in the container, where the density and the effective atomic number will be assessed. Typically, to obtain a better accuracy the density and the effective atomic number will be assessed at more than one location.
4. The path length (height of the liquid body) at the coordinates specified at 3. Both the coordinates and the path length values are obtained from the processing at step 726.

Step 2702 receives the HI and the Lo image information as well as the coordinates where the density and effective atomic numbers will be assessed. The processing at step 2702 will essentially extract from the HI and the Lo images the grey level values at each of the coordinates. If each coordinate is larger than a single pixel, say it encompasses several pixels in the HI and the Lo images, then the grey level extraction could include averaging the grey level values encompassed within each coordinate area. Therefore, the processing at step 2702 outputs two sets of grey level values, the first set extracted from the HI image and the second extracted from the Lo image.

The two sets of grey level values are handled by the process at step 2704. That step computes the X-ray attenuation coefficients for each of the coordinates. So, in addition to the grey level values sets, the process at step 2704 also receives the path length values from step 2700, where each path length value is associated to a given coordinate. As mentioned above, a given path length value is essentially the thickness of the body of fluid through which the X-rays pass. Note that the path length is not necessarily the same for all the coordinates.

The processing at step 2704 applies the following algorithm for computing the attenuation coefficient for the various coordinates at the HI energy level:

$$\mu_{Hi_{1...n}} = \frac{1}{XPL_{1...n}} \times \text{Ln}\left(\frac{E_{Hi(bgnd)}}{E_{Hi(final)_{1...n}}}\right)$$

Where:
1. $\mu_{Hi_{1...n}}$ is the attenuation coefficient at the HI energy level for the coordinates 1 . . . n;
2. $XPL_{1...n}$ is the path length at coordinates 1 . . . n for the HI energy level;
3. $E_{Hi(bgnd)}$ at coordinates 1 . . . n for the HI energy level;
4. $E_{Hi(final)_{1...n}}$ are the grey level values at coordinates 1 . . . n for the HI energy level.

A similar equation is used to compute the attenuation coefficients at the various coordinates at the Lo energy level.

$$\mu_{Lo_{1...n}} = \frac{1}{XPL_{1...n}} \times \text{Ln}\left(\frac{E_{Lo(bgnd)}}{E_{Lo(final)_{1...n}}}\right)$$

Where:
1. $\mu_{Lo_{1...n}}$ is the attenuation coefficient at the HI energy level for the coordinates 1 . . . n;
2. $XLP_{1...n}$ is the path length at coordinates 1 . . . n for the HI energy level;
3. $E_{Lo(bgnd)}$ at coordinates 1 . . . n for the HI energy level;
4. $E_{Lo(final)_{1...n}}$ are the grey level values at coordinates 1 . . . n for the HI energy level.

The processing continues at steps 2706 and 2708 that compute the density of the liquid and the effective atomic number of the liquid at the respective coordinates. The density computation at step 2706 receives as input the X-ray attenuation coefficients, and machine calibration constants. Specifically, the density computation is effected by using the following algorithm:

$$\rho_{1...n} = \frac{(a_{Hi} \times \mu_{Lo_{1...n}}) - (a_{Lo} \times \mu_{Hi_{1...n}})}{(a_{Hi} \times b_{Lo}) - (a_{Lo} \times b_{Hi})}$$

Where:
1. $\rho_{1 \ldots n}$ is the density of the liquid at the coordinates 1 ... n. Note that the density computation uses grey level information from both the HI and the Lo X-ray images;
2. $a_{Hi}$, $a_{Lo}$, $b_{Hi}$, $b_{Lo}$ are X-ray imaging system constants. These constants are stored in the memory 302 of the processing module 200;
3. $\mu_{Lo_{1 \ldots n}}$ is the attenuation coefficient at the HI energy level for the coordinates 1 ... n;
4. $\mu_{Hi_{1 \ldots n}}$ is the attenuation coefficient at the HI energy level for the coordinates 1 ... n.

Step 2708 computes the effective atomic number at the coordinates 1 ... n. This computation also makes use of the attenuation coefficients computed earlier for the HI and Lo energy levels and also uses the X-ray imaging system constants. Specifically, the following algorithm can be used to perform the computation:

$$Z_{eff1 \ldots n} = 2.94 \sqrt{\frac{(-b_{Hi} \times \mu_{Lo_{1 \ldots n}}) + (b_{Lo} \times \mu_{Hi_{1 \ldots n}})}{(a_{Hi} \times \mu_{Lo_{1 \ldots n}}) - (a_{Lo} \times \mu_{Hi_{1 \ldots n}})}}$$

Where:
1. $Z_{eff_{1 \ldots n}}$ is the effective atomic number of the liquid measured at the coordinates 1 ... n;
2. $a_{Hi}$, $a_{Lo}$, $b_{Hi}$, $b_{Lo}$ are X-ray imaging system constants. These constants are stored in the memory 302 of the processing module 200;
3. $\mu_{Lo_{1 \ldots n}}$ is the attenuation coefficient at the HI energy level for the coordinates 1 ... n;
4. Is the attenuation coefficient at the HI energy level for the coordinates 1 ... n.

Finally, step 2710 outputs the density and the effective atomic number for each or the 1 ... n coordinates.

Figure 28:
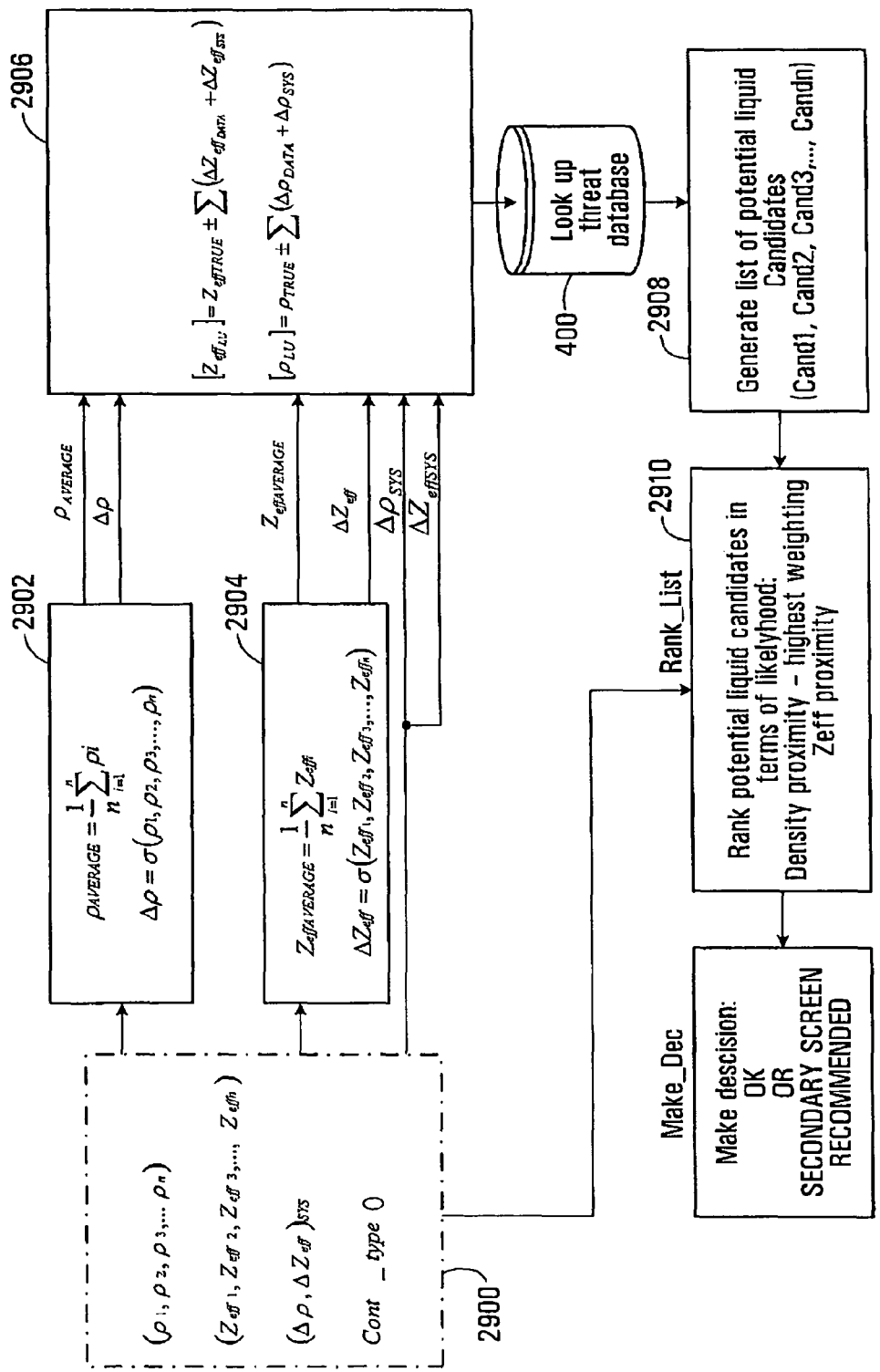
FIG. 28 is a flowchart of a process for determining threat assessment of a liquid.

Referring back to the flowchart of FIG. 7, the computation of the density and the effective atomic number at step 738 leads to step 741 where a determination is made as to whether or not the product that was scanned by the X-ray imaging system is a security threat. This determination will be described in greater detail in connection with the flowchart on FIG. 28. The process starts at step 2900. The processing at step 2900 receives the following information:
1. $Z_{eff_{1 \ldots n}}$ is the effective atomic number of the liquid measured at the coordinates 1 ... n, as computed at step 738.
2. $\rho_{1 \ldots n}$ is the density of the liquid at the coordinates 1 ... n, also as computed at step 738.
3. ($\Delta\rho$, $\Delta_{eff}$) which is the system error or standard error generated by the system itself.

Step 2902 computes an average density value for the liquid and also the standard deviation. Specifically, the average density is determined by, $$\rho_{average} = \frac{1}{n}\sum_{i=1}^{n}\rho_i$$

Where:
1. $\rho_{average}$ is the average density of the liquid.

Step 2902 also computes the standard deviation $\Delta\rho$ of $\rho_{1 \ldots n}$ with relation to $\rho_{average}$. The standard deviation is expressed by $\Delta\rho = \sigma(\rho_1, \rho_2, \rho_3, \ldots \rho_n)$.

Similarly, step 2904 computes the average effective atomic number along with the standard deviation. Specifically, the average effective atomic number is determined by:

$$Z_{eff-average} = \frac{1}{n}\sum_{i=1}^{n}Z_{eff_i}$$

Where:
1. $Z_{eff-average}$ is the average effective atomic number of the liquid.

Step 2904 also computes the standard deviation $\Delta Z_{eff}$ of $Z_{eff_{1 \ldots n}}$ with relation to $Z_{eff-average}$. The standard deviation is expressed by $\Delta Z_{eff} = \sigma(Z_{eff_1}, Z_{eff_2}, Z_{eff_3}, \ldots Z_{eff_n})$.

Steps 2902 and 2904 output to step 2906, which is the next step in the processing thread, $\rho_{average}$, $\Delta\rho$, $Z_{eff-average}$, $\Delta Z_{eff}$, $\Delta\rho_{sys}$ and $\Delta Z_{eff-sys}$.

Step 2906 generates density and effective atomic number lookup values to query the knowledge bank 400. More specifically, the processing at step 2906 computes an effective atomic number lookup window to select potential matching candidates in the knowledge bank 400. This lookup window is mathematically defined as:

$$[Z_{eff-LU}] = Z_{eff-average} \pm \rho(\Delta Z_{eff} + \Delta Z_{eff-sys})$$

The lookup window is defined by a low effective atomic number value $Z_{eff-LU-Low}$ and by a high effective atomic number value $Z_{eff-LU-HI}$.

The density lookup window is mathematically defined as: $[\rho_{LU}] = \rho_{average} \pm \Sigma(\Delta\rho + \Delta\rho_{sys})$. The lookup window is defined by a low effective density value $\rho_{LU-low}$ and by a high effective atomic number value $\rho_{LU-high}$.

The knowledge bank 400 is queried on the basis of the density and effective atomic number lookup windows. The selection process is such that a product in the knowledge bank 400 for which an effective atomic number and a density value fall in the respective lookup windows are retained as potential candidates. The list of candidates is then processed at step 2910 that determines if the liquid poses a security threat. More specifically, the processing at step 2910 tries to determine to what degree anyone of the candidates matches the characteristics of the product scanned by the X-ray imaging system.

A "candidate" is essentially an entry in the knowledge bank 400. Most of those entries are likely to be associated to commercially available products such as product for human consumption (water, juice, soft drinks, etc.) and personal hygiene product (shampoo, toothpaste, deodorant, skin care cream, washing gel, etc.), among others that passengers are likely to have in hand carried baggage. As discussed earlier, each candidate that is selected at step 2908 is defined by certain characterizing information, such as density, effective atomic number and container characterization among others. This characterizing information is then compared with the product characterization effected as a result of the X-ray scan to determine if a match can be found. If a match exists, this means that in all likelihood the liquid in the container that was scanned by the X-ray imaging system is "genuine" in other words matches the labelling on the container. So, if the product that is being scanned is a liquid filled container, where the container is labelled as a bottle of water, a match would indicate that in all probability the liquid is water and has not been substituted by something else.

The process for determining if the product characterization matches any one of the candidates involves comparing the product characterization with the information that characterizes each candidate. In a specific and non-limiting example of implementation, a first comparison is made between the density (as computed from the X-ray images) of the scanned product and the density information for each one of the candidates. The candidate that matches best the density of the scanned product is retained. Next, the effective atomic number (as computed from the X-ray images) of the product is compared to the effective atomic number of the candidate that was retained. If a match is found then the final step of the assessment includes comparing the container features identified from the X-ray images with the container features stored for that candidate in the knowledge bank 400. If a match is found then the system concludes that the product that was scanned by the X-ray imaging system is authentic and corresponds to the candidate.

The decision as to whether or not the scanned product is a security threat depends on the nature of the candidate. If the candidate is identified in the knowledge bank 400 as being "safe" then scanned product is deemed safe too. On the other hand, if the scanned product matches a candidate that is deemed "illegal" such as for example a flammable liquid or another dangerous chemical, then the scanned product would be deemed "unsafe".

In instances where no match can be found between the scanned product and a candidate, which occurs when the effective atomic number of the best candidate (the candidate retained subsequent to the density comparison) does not match the effective atomic number of the scanned product, or when the container characterization of the best candidate does not match the container characterization of the scanned product, the system assumes that the scanned product is suspect and triggers an alert. This situation would occur if a passenger would be attempting to pass at the security check point a container labelled as a common "safe" product such as a soft drink bottle, in which the soft drink has been replaced by another liquid, which has a different density and/or effective atomic number than the soft drink.

There are many other threat assessment strategies that can be used without departing from the spirit of the invention. For instance, the knowledge bank 400 can be augmented to include scattering/diffraction signatures of the various entries stored therein. In this fashion, the system would be provided with an additional parameter that can be used to decide if a match exists between the scanned product and anyone of the knowledge bank 400 entries.

Note that in instances where the container of the scanned product can be alone used to identify a specific entry in the knowledge bank 400, then the threat assessment process at step 2910 would be greatly simplified since a candidate exists to which the scanned product is being compared.

After the threat assessment has been completed, the system issues via the user interface the decision, which in one example could be a simple "pass" indicating that the product is safe or "fail" indicating that no match was found which would prompt a rejection of the product (the passenger would not be allowed to proceed with it) or a manual search/inspection in an attempt to identify with greater precision the nature of the product.

Figure 19A:
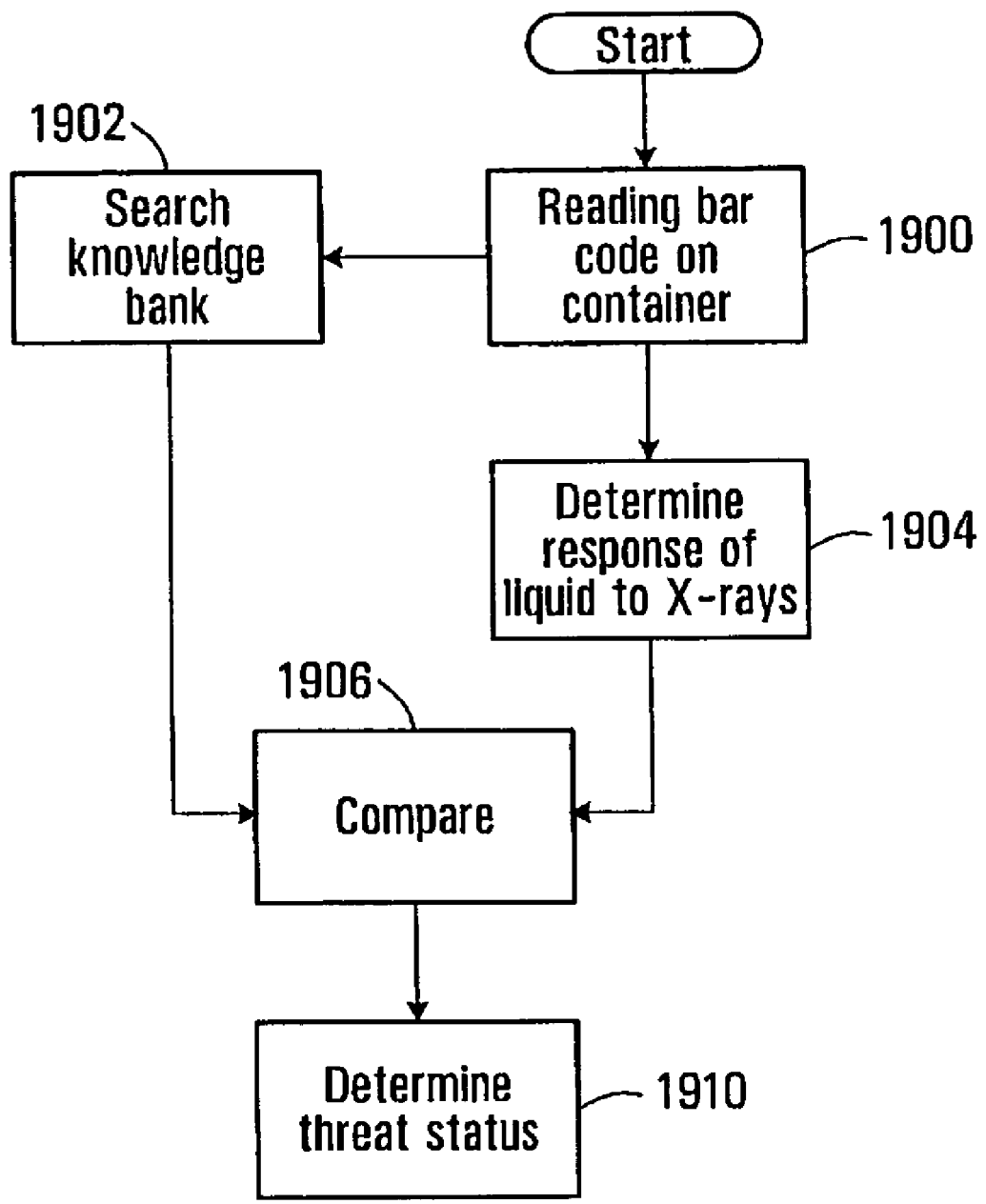
FIG. 19a is a detailed block diagram of a second non-limiting example of implementation of the process shown in FIG. 3.

The flow chart in FIG. 19*a* illustrates another example of implementation of the invention where the characterization of the product is made by reference to the Universal Product Code (UPC) bar code that appears on the product. Nearly all the products that are sold today in the market use a bar code system that facilitate checkout procedures and also help tracking inventories. UPC barcodes originate with the Uniform Product Council that is manages the allocation of the barcodes to different manufacturers. A typical bar code that is applied to the product package has generally two components; one is the machine readable part and the other the human readable part. The machine readable part appears as a series of bars while the human readable part is a series of digits appearing below the machine readable bars. A typical UPC bar code has a part that identifies the manufacturer and another part that identifies the actual product within that manufacturer's product line. Since UPC barcodes are used primarily for payment and inventory control purposes they are unique for each product. Accordingly, the UPC barcode constitutes a unique identifier for almost every product that is found in market today.

The process at the flowchart of FIG. 19*a* starts at step 1900 where the bar code of the product (container+liquid) whose security status is to be established is read. This operation is performed by using a standard bar code reader of a type known in the art. The information obtained as a result of the reading operation is then used to search a knowledge bank 1902 and usually will be sufficient to uniquely identify the product among the plurality of products stored in the knowledge bank 1902.

The structure of the knowledge bank is shown in FIG. 19*b*. The information in the knowledge bank 1908 can be organized as a table. Each entry of the table is associated with a certain liquid product. Typically, the products in the table are those that are most likely to be carried by passengers a security checkpoint. Examples include bottled water, soft drinks, and juice and cosmetic/healthcare products, among others. Each entry of the knowledge bank is identified by the UPC bar code applied on the product by its manufacturer. Since bar codes are unique, that entry conveniently constitutes a key on the basis of which the knowledge bank 1908 can be searched. In the specific example of implementation shown at FIG. 19*b*, the knowledge bank 1908 has seven data fields for each entry. The data fields are as follows:

1) The UPC bar code that is expressed in any suitable format.
2) The density of the liquid. The density may be the real density (as measured by standard techniques) or the density as assessed as a result of an X-ray scan, or both. In this example, only one density value is shown assuming that the real density and the one obtained as a result of an X-ray scan are the same.
3) The effective atomic number of the liquid as measured by X-rays.
4) Container features, such as visual characteristics that distinguish the container. Examples include the dimensions of the container (height and transverse dimensions), type of container (screw cap, can or other), general container shape (cylindrical, rectangular cross-section, etc), and unique visual features such as ridges or projections on the walls, among many others. One possibility is to store in this data field a 3d image of the product that would show the product from different sides. With the appropriate image viewer, the operator can, therefore be provided with a complete image of the product that was found to match the barcode search operation. The container features also include information on the wall thickness and the material from which the wall is made such as to allow compensating the X-ray image data for the attenuation by the container walls.
5) The diffraction/back scatter signature.
6) The product identification. This could be the name/brand of the product, as it appears on the label of the product. The information can be stored as an image of the label to allow the operator to see on a computer screen how the label looks.
7) The threat status. This indicates if the product is safe or not safe. For instance, the first three products in the table are common household items that crate no danger. Accordingly, if the screening operation confirms that products carried by passengers at the security check point correspond to anyone of those entries, then the products are deemed safe. On the other hand if a product is identified as matching the last entry, namely a strong acid, an alarm should be triggered on the basis of the fact that the product is not allowed beyond the checkpoint.

It should be recognized that the structure of the knowledge bank 1908 can include more information about liquid products or less information, without departing from the spirit of the invention.

Referring back to FIG. 19*a*, step 1904 determines the response of the liquid in the container to penetrating radiation, X-rays in particular. This can be done in the same way as described previously under the first example of implementation. In short, step 1904 will derive parameters of the liquid from the X-ray scan, such as density, effective atomic number, and diffraction/back scatter signature, among others. This can be done by referring or using information stored in the knowledge bank 1908, such as for example the thickness of the container wall and the material from which the container wall is made such as to perform X-ray image compensation for the attenuation of the X-rays by the container wall.

Next, the comparison step 1906 determines the threat status of the liquid product. This is done by comparing parameters of the liquid product as extracted from the knowledge bank to those measured by the X-ray scan. Assume for the sake of this example, that at step 1900 the bar code on the container was correctly read and the search step 1902 identified an entry in the knowledge bank on the basis of the bar code. The comparison step 1906 will then read the data associated with this entry, such as the density and effective atomic number of the liquid, the container features, diffraction/back scatter signature, product information and threat status. Next, step 1906 will compare the parameters such as the density, effective atomic number and/or diffraction/backscatter signature to the parameters that were assessed by the X-ray inspection.

The results of the comparison are passed to step 1910 that performs the threat assessment. If there is a match between the parameters read from the knowledge bank and those measured by the X-ray inspection machine, then the process assumes that the container that is being inspected contains a liquid that is consistent with the label on the container; in other words the liquid in the original container has not been substituted by something else. Accordingly, if no substitution has been made and the container contains the original product, then the threat assessment step displays or otherwise communicates to the operator the threat status from the matching entry in the knowledge bank. For instance if the matching entry is associated with a product that has "safe" threat status, then the step 1910 will conclude that the product can be carried beyond the check point. Otherwise, when the matching entry is associated with an "unsafe" product the step 1910 will notify the security operator accordingly.

On the other hand, if no match is found between the parameters read from the knowledge bank and those measured by the X-ray inspection machine, the logic concludes that the liquid in the container is different from what the label says. This is a strong indication that the original liquid has been substituted by something else, in which case the product is deemed "unsafe".

Figure 20:
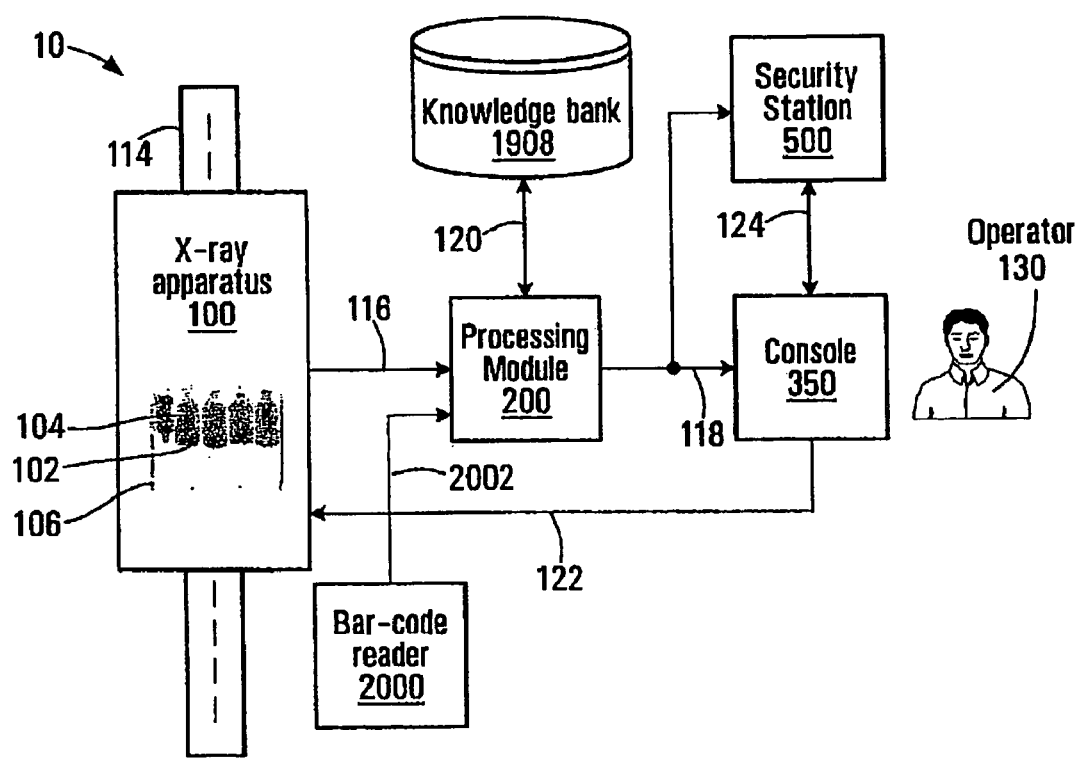

FIG. 20 is a block diagram of the equipment used to implement the method described in FIG. 19*a*. The installation is very similar to the set-up described in connection with FIG. 1 and for that reason whenever possible similar reference numbers will be used. The main distinction resides in the addition of a bar code reader 2000 that generates a bar code signal on output 2002 conveying the bar codes scanned by the reader 2000. The output 2002 connects to the processing module 200.

In this example of implementation the bar code reader 2000 is separate from the X-ray apparatus 100. Specifically, the bar code reader 2000 may be a hand-held reader of the type commonly used at checkout payment stations, in stores. Alternatively, the bar code reader 2000 may be a stationary device that has a reading window. The container is presented in front of the reading window to allow the bar code to be read.

In the case of a hand held bar code reader 2000, the operator 130 would scan the liquid product whose threat level is to be assessed such as to read the bar code. Once the bar code is acquired, the knowledge bank 1908 is searched by the processing module 200 to locate the entry associated with that code. If the entry in the knowledge bank 1908 is identified, information about the entry can be displayed on the operator console 350. For instance one or more container features can be visually shown on the console 350, such as a three-dimensional image of the container, allowing the operator to visually confirm that the entry in the knowledge bank 1908 indeed matches the container that was scanned.

Next, the operator 130 processes the container as discussed earlier. In particular, the liquid product is placed in the tray and the tray put on the conveyor belt of the X-ray apparatus 100. The X-ray scan is performed and the results are passed to the processing module 200. The processing module will process the X-ray image data to extract the response of the liquid in the container to the X-rays. The response is compared to the parameters stored in the previously identified knowledge bank 1908 entry.

The results of the threat assessment performed by the processing module 200 can then be displayed on the operator console 350.

In the instance where the bar code reader is a fixed device, it can be integrated in the X-ray apparatus such that the bar code on each container is read as the liquid product is put on the conveyor belt. This may require positioning the containers in the tray in such a way as to leave the bar codes exposed.

The reader will appreciate that many options exist to position the bar code reader in a way to suit a wide variety of possible applications.

In a possible variant, the bar code reader can be replaced with a Radio Frequency Identification (RFID) tags reader, suitable for liquid products that use such RFID tags for identification purposes. More specifically, RFID tags have an antennae and a small electronic circuit holding the information to supply when the RFID tag is interrogated. RFID tags can be read over relatively short distances (10 feet or less) and the reading does not have to be in the line of sight of the reader. In this type of application the liquid product to be scanned may be passed close to an RFID tag reader that will gather the identifying information. For instance, the RFID tag reader may be integrated to the X-ray apparatus 100 adjacent the conveyor of the X-ray apparatus. As the liquid product is put in the tray on the conveyor the liquid product will pass close enough the RFID tag reader for the reading operation to take place.

It is desirable to provide a knowledge bank 1908 that is as extensive as possible. In this fashion, most of the liquid products that a passenger is likely to carry through the security checkpoint can be referenced to an entry in the knowledge bank, allowing to precisely determine if the liquid product is a threat or not. Building the knowledge bank 1908 would involve gathering the necessary information for a wide variety of liquid products and then entering that information in the database that would constitute the knowledge bank 1908.

Gathering the initial information may be done by purchasing the liquid products that should be referenced in the knowledge bank 1908 and performing an analysis to obtain the necessary data. For instance, for each product the bar code on the container is read with a bar code reader and the information stored. Next the container is analysed to generate the various features of interest that are to be stored in the knowledge bank 1908, such as its visual features, container wall thickness and material from which the container wall is made. Finally, the response of the liquid product to X-rays is determined and the resulting parameters such as density, effective atomic number and/or diffraction/scattering signature obtained.

One simplified way of obtaining the response of the liquid to X-rays is to process the liquid product in the X-ray apparatus 100 as per the process described in the flowchart of FIG. 7. Once the container walls thickness and container wall material is known, the computation of the liquid density, effective atomic number and/or diffraction scattering signature can be made on the basis of the information contained in the X-ray image.

The information generated as a result of this initial data gathering is loaded in the knowledge bank 1908, which as discussed previously, is in the form of a database. The database can be structured in any suitable fashion, on any suitable computer readable medium, without departing from the spirit of the invention.

In use, the system shown in FIG. 1a or 20 would be operated at security check points such as at airports. The entity that operates the units would normally be a government agency or a private contractor mandated by the government to enforce security at the checkpoints. In order to perform adequately, the system should be updated regularly to keep knowledge bank 1908 current. Specifically, the knowledge bank 1908 should be updated periodically to reference new liquid products that are being released on the market and that are susceptible to be carried by passengers through the security checkpoint.

Figure 21:
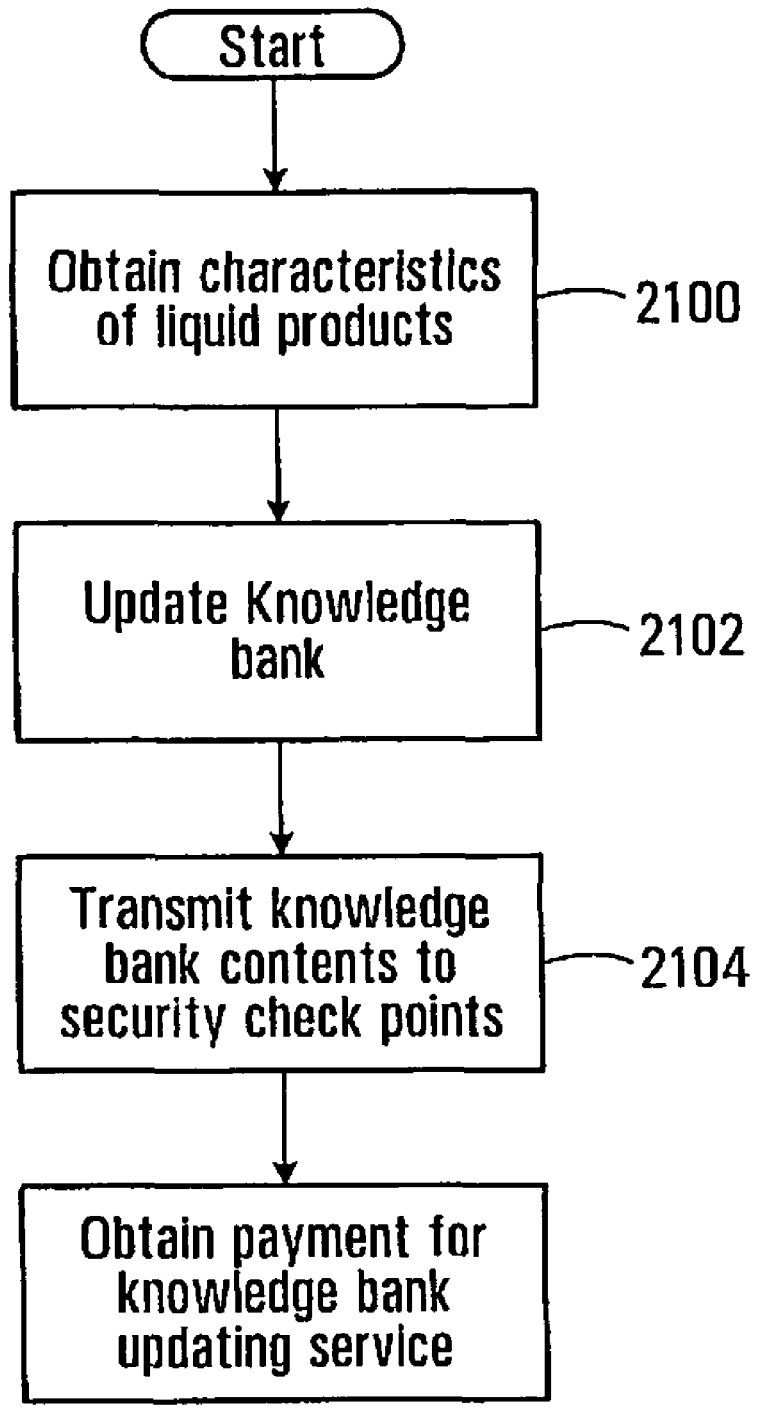
FIG. 21 is a detailed block diagram of a third non-limiting example of implementation of the process shown in FIG. 3.

The knowledge bank updating information is illustrated by the flowchart on FIG. 21. Initially, a list is obtained on the new products that have been recently commercialized and that should be loaded in the knowledge bank 1908. This can be done in various ways. For instance, manufacturers of products that are most likely to be carried through the check point may be queried to determine what are the new products that have been released in the market since the last knowledge bank 1908 update cycle. Once the list of those products is set, then samples are obtained. At step 2100 the samples are processed as discussed previously to extract the relevant data. The relevant data is then loaded in the knowledge bank 1908, at step 2102

The knowledge bank 1908, either in its entirety or only the updated part is transmitted to the various locations that use it to perform security screening. The transmission can be done electronically, such as over the Internet or manually by recording the update on a portable machine readable medium, which is then loaded in a reader on the computer that manages the knowledge bank 1908. This operation is shown at step 2104. The number of locations that need to be updated will depend upon the manner in which the individual security checkpoints work. If each security checkpoint is a stand alone unit and has its own knowledge bank 1908, then each security checkpoint has to be updated individually. On the other hand, if the security checkpoints are networked, a more automated updating procedure is possible. For instance, if the network is such that a common knowledge bank 1908 is provided which services a plurality of security checkpoints, then a single update is sufficient. On the other hand, if the networked arrangement uses a plurality of knowledge banks local to the respective security checkpoints, then the data to perform the update can be electronically sent in the field to the various security checkpoints to make local updates.

The knowledge bank update would normally be in the form of a subscription or available on demand. In this fashion the entity that performs the knowledge bank 1908 update will charge the end user (government entity or private contractor) for the updates. The financial arrangements can vary and many may be in the form of a fixed fee arrangement valid for a predetermined time period, say one year. During the subscription period the end user receives automatically updates, as soon as they become available. When the update is done on demand, then an update is sent only when requested and a payment is made by the end user after reception of the service.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. Method for performing security screening at a security checkpoint, comprising:
    a) performing an X-ray inspection on hand carried baggage and on a liquid product comprised of a container holding a liquid while the liquid product remains outside the hand carried baggage with a same X-ray imaging device, the X-ray inspection generating X-ray image data of the hand carried baggage and X-ray image data of the liquid product;
    b) processing the X-ray image data of the hand carried baggage to render an image of the hand carried baggage on a display to assist an operator in determining if the baggage contains illegal objects;
    c) processing with a computer the X-ray image data of the liquid product, the computer being programmed with software to:
        i) derive path length information based at least in part on the X-ray image data of the liquid product, the path length information being an approximation of a distance travelled by an X-ray through the liquid of the liquid product;
        ii) use the derived path length information to determine if the liquid held in the container is a security threat.

2. A method as defined in claim 1, wherein the X-ray imaging device includes a conveyor belt on which objects to be inspected are placed and which transports the objects through the X-ray imaging device, said method including placing the hand carried baggage and the liquid product on the conveyor belt such that the hand carried baggage and the liquid product are carried through the X-ray imaging device while the liquid product remains outside the hand carried baggage.

3. A method as defined in claim 2, including placing the liquid product on the conveyor belt in a tray.

4. A method as defined in claim 3, wherein processing the X-ray image data of the liquid product includes compensating the X-ray image data of the liquid product for an attenuation of X-rays due to the tray.

5. A method as defined in claim 2, wherein processing the X-ray image data of the liquid product includes communicating with a data storage medium which stores machine readable data conveying information about characteristics of a plurality of reference liquid products.

6. A method as defined in claim 5, wherein processing the X-ray image data of the liquid product includes searching the data storage medium at least in part based on the information derived from the X-ray image data of the liquid product.

7. A method as defined in claim 6, wherein the data storage medium includes a plurality of entries, each entry containing information about one or more characteristics of a reference liquid product, and wherein processing the X-ray image data of the liquid product includes attempting to match the liquid product to at least one of the entries at least in part based on the information derived from the X-ray image data of the liquid product.

8. A method as defined in claim 7, wherein each entry in the data storage medium is associated with a respective reference liquid product, each entry conveying information about the container of the reference liquid product to which the entry is associated.

9. A method as defined in claim 8, wherein the information about the container includes container shape information.

10. A method as defined in claim 8, wherein the information about the container includes container cross-sectional profile information.

11. A method as defined in claim 8, wherein the information about the container includes container height information.

12. A method as defined in claim 8, wherein the information about the container includes container width information.

13. A method as defined in claim 8, wherein the information about the container indicates if the container has a screw cap.

14. A method as defined in claim 8, wherein the information about the container includes information about the container wall.

15. A method as defined in claim 14, wherein the information about the container wall includes container wall thickness information.

16. A method as defined in claim 7, wherein each entry in the machine readable storage medium is associated with a respective reference liquid product comprised of a container holding a liquid and conveying information about the liquid held in the container.

17. A method as defined in claim 2, wherein processing the X-ray image data of the liquid product includes compensating the X-ray image data of the liquid product for an attenuation of X-rays due to the conveyor belt.

18. A method as defined in claim 1, wherein the X-ray image data of the liquid product conveys a two-dimensional image of the container.

19. A method as defined in claim 1, wherein processing the X-ray image data of the liquid product includes determining a parameter of the liquid held in the container at least in part based on information conveyed by the X-ray image data of the liquid product, the parameter being selected from a set consisting of a density, an effective atomic number and an attenuation coefficient.

20. A method as defined in claim 18, wherein processing the X-ray image data of the liquid product includes determining a parameter of the liquid held in the container at least in part based on information conveyed by the X-ray image data of the liquid product, the parameter being selected from a set consisting of a density, an effective atomic number and an attenuation coefficient.

21. A method as defined in claim 1, wherein processing the X-ray image data of the liquid product includes compensating the X-ray image data of the liquid product for an attenuation of X-rays due to walls of the container of the liquid product.

22. A system for performing security screening at a security checkpoint on hand-carried baggage and on liquid products, said system comprising:
   a) an X-ray imaging device for performing an X-ray inspection on hand carried baggage and on liquid products, said X-ray imaging device generating X-ray image data;
   b) a processor module in communication with the X-ray imaging device for receiving X-ray image data generated by said X-ray imaging device, said X-ray image data including X-ray image data associated with a liquid product and X-ray image data associated with a piece of hand carried baggage, the liquid product being comprised of a bottle holding a liquid, said processor module being programmed for:
     i) processing the X-ray image data associated with the piece of hand carried baggage to generate an image signal;
     ii) processing X-ray image data associated with the liquid product to:
       (1) derive path length information based at least in part on the X-ray image data associated with the liquid product, the path length information being an approximation of a distance travelled by an X-ray through the liquid of the liquid product;
       (2) process the path length information to determine if the liquid held in the container is a security threat;
   c) an output including a display in communication with the processor module for:
     i) rendering an image of the hand carried baggage based on the image signal to assist an operator in detecting an illegal object in the hand carried baggage; and
     ii) displaying a notification on the display conveying results obtained when determining if the liquid held in the container is a security threat.

23. A system as defined in claim 22, wherein the X-ray imaging device includes a conveyor belt on which liquid products and hand carried baggage are placed and which transports the objects through the X-ray imaging device.

24. A computer readable storage medium storing a program element suitable for execution by a computing apparatus for performing security screening at a security checkpoint on hand-carried baggage and on a liquid product, the liquid product being comprised of a container holding a liquid, said computing apparatus comprising:
   a) a memory unit;
   b) a processor operatively connected to said memory unit, said program element when executing on said processor being operative for:
     i) receiving X-ray image data of the hand carried baggage and X-ray image data of the liquid product, said X-ray image data being generated by performing an X-ray inspection with a same X-ray imaging device on the hand carried baggage and on the liquid product while the liquid product remains outside the baggage;
     ii) processing the X-ray image data of the hand carried baggage to render an image of the hand carried baggage on a display to assist an operator in determining if the baggage contains illegal objects;
     iii) processing the X-ray image data of the liquid product to:
       (1) derive path length information based at least in part on the X-ray image data of the liquid product, the path length information being an approximation of a distance travelled by an X-ray through the liquid of the liquid product; and (2) use the derived path length information to determine if the liquid held in the container is a security threat.

25. A computer readable storage medium as defined in claim 24, wherein processing the X-ray image data of the liquid product includes communicating with a data storage medium which stores machine readable data conveying information about characteristics of a plurality of reference liquid products.

26. A computer readable storage medium as defined in claim 25, wherein processing the X-ray image data of the liquid product includes searching the data storage medium on the basis of the information derived from the X-ray image data of the liquid product.

27. A computer readable storage medium as defined in claim 26, wherein the data storage medium includes a plurality of entries, each entry containing information about one or more characteristics of a reference liquid product, and wherein processing the X-ray image data of the liquid product includes attempting to match the liquid product to at least one of the entries on the basis of the information derived from the X-ray image data of the liquid product.

28. A computer readable storage medium as defined in claim 27, wherein each entry in the data storage medium is associated with a respective reference liquid product, each entry conveying information about the container of the liquid product to which the entry is associated.

29. A computer readable storage medium as defined in claim 28, wherein the information about the container includes container shape information.

30. A computer readable storage medium as defined in claim 28, wherein the information about the container indicates if the container has a screw cap.

31. A computer readable storage medium as defined in claim 28, wherein the information about the container includes information about the container wall.

32. A computer readable storage medium as defined in claim 31, wherein the information about the container wall includes container wall thickness information.

33. A computer readable storage medium as defined in claim 24, wherein the X-ray image data of the liquid product conveys a two-dimensional image of the container.

34. A computer readable storage medium as defined in claim 33, wherein processing the X-ray image data of the liquid product includes determining a parameter of the liquid held in the container at least in part based on information conveyed by the X-ray image data of the liquid product, the parameter being selected from a set consisting of a density, an effective atomic number and an attenuation coefficient.

35. A computer readable storage medium as defined in claim 24, wherein processing the X-ray image data of the liquid product includes determining parameter of the liquid held in the container at least in part based on information conveyed by the X-ray image data of the liquid product, the parameter being selected from a set consisting of a density, an effective atomic number and an attenuation coefficient.

36. A computer readable storage medium as defined in claim 24, wherein the X-ray imaging device includes a conveyor belt on which the hand carried baggage and the liquid product are placed and which transports the hand carried baggage and the liquid product through the X-ray imaging device, wherein processing the X-ray image data of the liquid product includes compensating the X-ray image data of the liquid product for an attenuation of X-rays due to the conveyor belt.

37. A computer readable storage medium as defined in claim 24, wherein processing the X-ray image data of the liquid product includes compensating the X-ray image data of the liquid product for an attenuation of X-rays due to walls of the container of the liquid product.

38. A computer readable storage medium as defined in claim 24, wherein the X-ray imaging device includes a conveyor belt on which the hand carried baggage and the liquid product are placed and which transports the hand carried baggage and the liquid product through the X-ray imaging device, wherein the hand carried baggage and the liquid product are supported by a tray when placed on the conveyor belt during the X-ray inspection, wherein processing the X-ray image data of the liquid product includes compensating the X-ray image data of the liquid product for an attenuation of X-rays due to the tray.

39. An apparatus for use in performing security screening at a security checkpoint on hand-carried baggage and on a liquid product, the liquid product being comprised of a container holding a liquid, said apparatus comprising:
  a) an input for receiving X-ray image data of the hand carried baggage and X-ray image data of the liquid product, said X-ray image data being generated by performing an X-ray inspection with a same X-ray imaging device on the hand carried baggage and on the liquid product while the liquid product remains outside the baggage;
  b) a processor programmed for:
    i) processing the X-ray image data of the hand carried baggage to render an image of the hand carried baggage on a display to assist an operator in determining if the baggage contains illegal objects;
    ii) processing the X-ray image data of the liquid product to:
      (1) derive path length information based at least in part on the X-ray image data of the liquid product, the path length information being an approximation of a distance travelled by an X-ray through the liquid of the liquid product; and
      (2) use the derived path length information to determine if the liquid held in the container is a security threat.

40. An apparatus as defined in claim 39, wherein processing the X-ray image data of the liquid product includes determining a parameter of the liquid held in the container at least in part based on information conveyed by the X-ray image data of the liquid product, the parameter being selected from a set consisting of a density, an effective atomic number and an attenuation coefficient.

41. An apparatus as defined in claim 39, wherein the X-ray imaging device includes a conveyor belt on which objects to be inspected are placed and which transports the objects through the X-ray imaging device, wherein processing the X-ray image data of the liquid product includes compensating the X-ray image data of the liquid product for an attenuation of X-rays due to the conveyor belt.

42. An apparatus as defined in claim 39, wherein processing the X-ray image data of the liquid product includes compensating the X-ray image data of the liquid product for an attenuation of X-rays due to walls of the container of the liquid product.

43. An apparatus as defined in claim 39, further comprising a memory unit for storing machine readable data conveying information about characteristics of a plurality of reference liquid products.

44. An apparatus as defined in claim 43, wherein said processor is programmed to determine if the liquid held in the container is a security threat at least in part by performing a search in the memory unit.

45. An apparatus as defined in claim 39, wherein the X-ray image data of the liquid product conveys a two-dimensional image of the container holding the liquid.

46. An apparatus as defined in claim 45, wherein said processor is programmed for processing the X-ray image data of the liquid product to determine a parameter associated with the liquid held in the container, the parameter being selected from a set consisting of a density, an effective atomic number and an attenuation coefficient.

47. An apparatus as defined claim 39, wherein
a) said X-ray image data is generated by positioning the liquid product on a tray while performing the X-ray inspection; and
b) said processor is programmed for processing the X-ray image data of the liquid product to compensate the X-ray image data of the liquid product for an attenuation of X-rays due to the tray.

* * * * *